United States Patent
Martakos et al.

(10) Patent No.: US 6,890,463 B2
(45) Date of Patent: May 10, 2005

(54) METHOD FOR TREATING EXPANDABLE POLYMER MATERIALS

(75) Inventors: Paul Martakos, Pelham, NH (US); Roger Labrecque, Londonderry, NH (US); Geoffrey Moodie, Nashua, NH (US); Steve A. Herweck, Nashua, NH (US); Theodore Karwoski, Hollis, NH (US)

(73) Assignee: Atrium Medical Corporation, Hudson, NH (US)

( * ) Notice: Subject to any disclaimer, the term of this patent is extended or adjusted under 35 U.S.C. 154(b) by 355 days.

(21) Appl. No.: 10/131,446

(22) Filed: Apr. 22, 2002

(65) Prior Publication Data

US 2003/0062650 A1 Apr. 3, 2003

Related U.S. Application Data

(63) Continuation-in-part of application No. 09/678,765, filed on Oct. 3, 2000, now Pat. No. 6,616,876.

(51) Int. Cl.[7] .......................... B29B 11/10; B29B 11/14; B29B 13/00; B29B 13/02; B29B 15/00
(52) U.S. Cl. ....................... 264/119; 264/122; 264/123; 264/126; 264/120; 264/241; 264/291
(58) Field of Search ................................ 264/122, 123, 264/119, 126, 120, 241, 291

(56) References Cited

U.S. PATENT DOCUMENTS

| | | | |
|---|---|---|---|
| 3,862,030 A | 1/1975 | Goldberg | 210/24 |
| 4,177,334 A | 12/1979 | Okita | 521/145 |
| 4,187,390 A | 2/1980 | Gore | 174/102 |
| 4,598,011 A | 7/1986 | Bowman | 428/221 |
| 4,938,911 A | 7/1990 | Bastiaansen et al. | 264/56 |

(Continued)

FOREIGN PATENT DOCUMENTS

| | | |
|---|---|---|
| EP | 106496 A2 | 4/1984 |
| EP | 288021 A2 A3 | 10/1988 |
| WO | WO 98/26731 A2 A3 | 6/1998 |
| WO | WO 00/12147 A1 | 3/2000 |
| WO | WO 01/15764 A1 | 3/2001 |
| WO | WO 01/21106 A1 | 3/2001 |
| WO | WO 01/82833 A2 A3 | 11/2001 |
| WO | WO 02/26279 A1 | 4/2002 |
| WO | WO 02/36054 A1 | 5/2002 |

OTHER PUBLICATIONS

Patent Abstracts of Japan, vol. 003, No. 109 (C–058), Sep. 12, 1979, JP 54086573 A (Nitto Electric Ind. Co. Ltd. (Jul. 10, 1979), abstract.
Patent Abstracts of Japan, vol. 018, No. 317 (M–1622), Jun. 16, 1994,; JP 06071744 A (Dai ichi Kogyo Seiyaku Co. Ltd.; Others: 01) (Mar. 15, 1994), abstract.
Libby, P. "Atherosclerosis; The New View" *Scientific American* 286(5):46–55 (May 2002).

*Primary Examiner*—Stephen J. Lechert, Jr.
(74) *Attorney, Agent, or Firm*—Lahive & Cockfield, LLP

(57) ABSTRACT

The invention is directed to methods involving rewetting of expandable polymers with a wettable liquid to allow for enhanced expansion at or below room temperature without breakage, and in some cases, allows one to achieve a greater expansion ratio than that allowed at elevated temperatures using known methods. The wettable liquid can be formed of a drug and/or an agent, such that the resulting polymer contains and emits the drug upon positioning at a target location of a patient body. The present invention also allows one to achieve material with unique properties and handling characteristics. These properties included decreased material thickness, increased density, an altered node/fibril morphology, and a more consistent web in the case of flat material. This method is not limited to room temperature conditions and can be applied whenever the expandable polymer material is wet with a wettable liquid, and the expansion is performed at a temperature preferably below the vaporization or boiling points of that liquid.

59 Claims, 25 Drawing Sheets

U.S. PATENT DOCUMENTS

| | | | | |
|---|---|---|---|---|
| 5,064,593 A | | 11/1991 | Tamaru et al. | 264/113 |
| 5,411,550 A | | 5/1995 | Herweck et al. | 623/1 |
| 5,476,589 A | | 12/1995 | Bacino | 210/500 |
| 5,552,100 A | | 9/1996 | Shannon et al. | 264/127 |
| 5,641,373 A | | 6/1997 | Shannon et al. | 156/242 |
| 5,721,283 A | | 2/1998 | Howard, Jr. et al. | 521/60 |
| 5,756,035 A | * | 5/1998 | Underwood et al. | 264/295 |
| 5,788,626 A | | 8/1998 | Thompson | 600/36 |
| 5,800,522 A | | 9/1998 | Campbell et al. | 623/1 |
| 5,824,050 A | | 10/1998 | Karwoski et al. | 623/1 |
| 5,843,173 A | | 12/1998 | Shannon et al. | 623/1 |
| 5,853,419 A | | 12/1998 | Imran | 606/191 |
| 5,897,587 A | | 4/1999 | Martakos et al. | 623/1 |
| 5,964,798 A | | 10/1999 | Imran | 623/1 |
| 5,976,169 A | | 11/1999 | Imran | 606/194 |
| 6,022,374 A | | 2/2000 | Imran | 623/1 |
| 6,030,428 A | | 2/2000 | Ishino et al. | 55/486 |
| 6,159,531 A | | 12/2000 | Dang et al. | 427/2.24 |
| 6,355,063 B1 | | 3/2002 | Calcote | 623/1.42 |
| 6,364,856 B1 | | 4/2002 | Ding et al. | 604/103.02 |
| 6,364,903 B2 | | 4/2002 | Tseng et al. | 623/1.15 |
| 6,368,626 B1 | | 4/2002 | Bhatt et al. | 424/473 |
| 6,613,082 B2 | | 9/2003 | Yang | |
| 6,613,084 B2 | | 9/2003 | Yang | |

\* cited by examiner

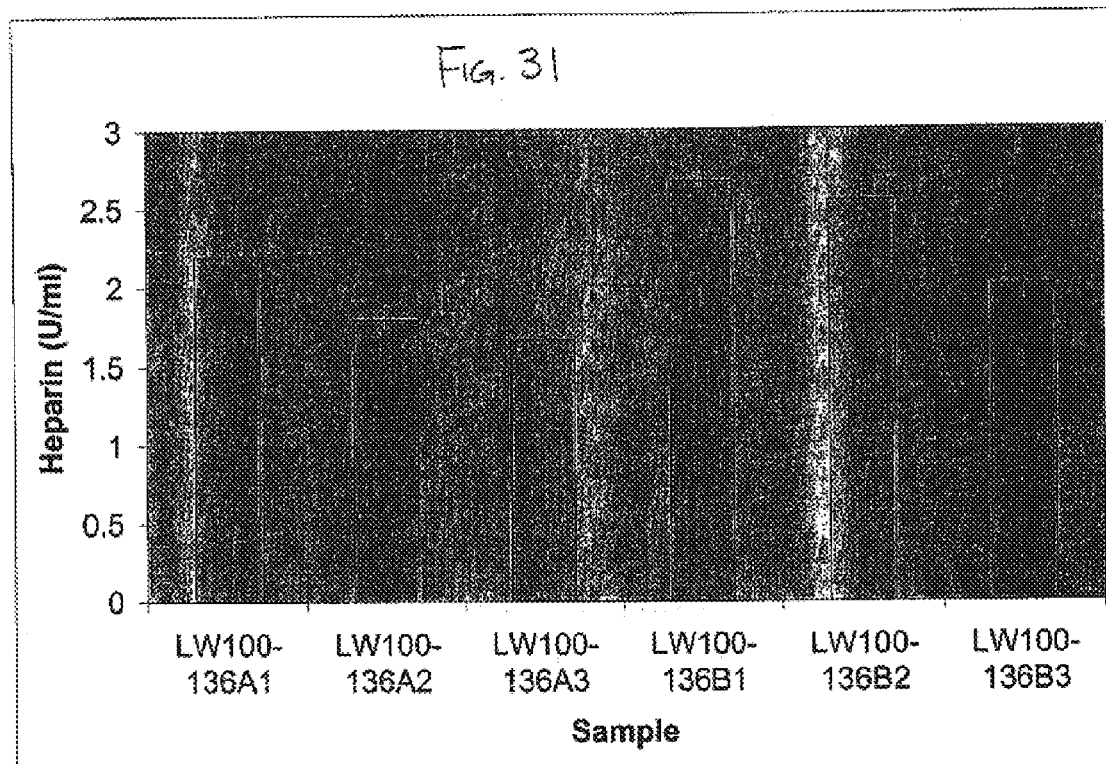

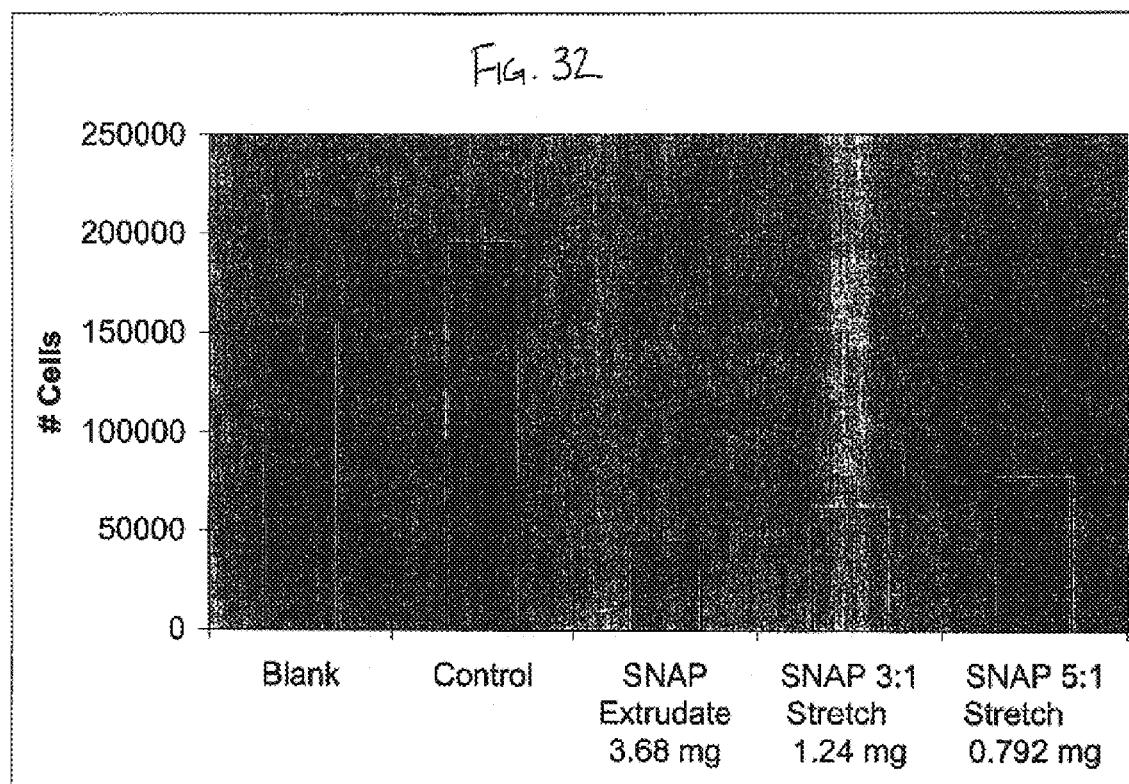

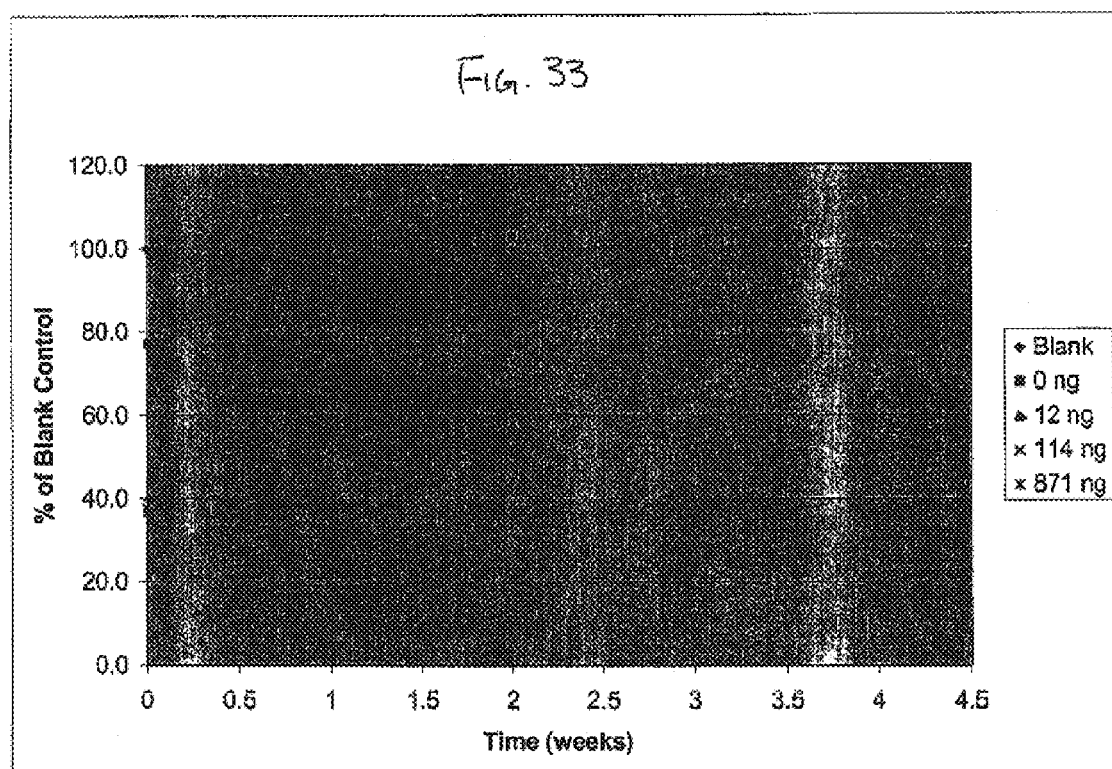

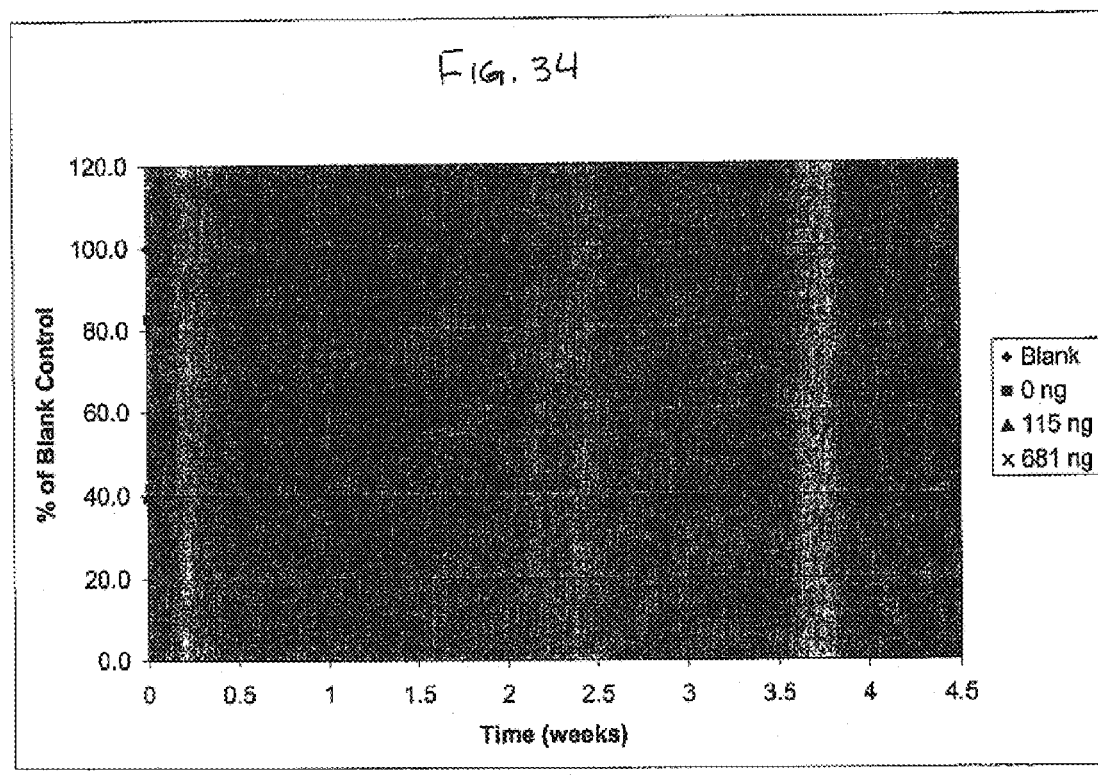

METHOD FOR TREATING EXPANDABLE POLYMER MATERIALS

RELATED APPLICATIONS

This application is a continuation-in-part of, and claims the benefit of, U.S. patent application Ser. No. 09/678,765, filed Oct. 3, 2000, now U.S. Pat. No. 6,616,876 which is expressly and entirely incorporated herein by reference.

TECHNICAL FIELD

The present invention relates generally to materials and processing of materials. More specifically, the present invention is directed to expandable polymers and methods for processing of expandable polymers.

BACKGROUND

A conventional method of forming an article made of an expandable polymer, such as PTFE, is to blend a powdered resin with a wettable liquid, such as a lubricant or extrusion aid, and compress the combination under relatively low pressure into a preformed billet. A wettable liquid is mixed with the powdered resin to control the degree of material shear that occurs during subsequent extrusion and to prevent excessive shear, which can damage the material.

Using a ram-type extruder, the billet is extruded through a die having a desired cross-section. Next, the wettable liquid is removed from the extruded material by drying or by another extraction method. The dried extruded material is then stretched in one or more directions at an elevated temperature below the crystalline melting point of the resin. In the case of PTFE, this results in the material taking on a microstructure characterized by elongated nodes interconnected by fibrils. Typically, the nodes are oriented with their elongated axis perpendicular to the direction of stretching.

According to conventional methods, there is a direct relationship between temperature and maximum expansion ratio while maintaining material uniformity and without breakage of the material. At low expansion temperatures, the material shows inconsistencies, is weak, and often breaks. Typically, heating well above room temperature is required to prevent the expandable polymer material from breaking and to ensure uniform material thickness after expansion.

U.S. Pat. No. 4,187,390 describes a method of forming porous PTFE that requires stretching at elevated temperatures. Material expanded at lower temperatures often fractures or results in weak material.

U.S. Pat. No. 5,552,100 describes a method of forming thin porous fluoropolymer films by post-sinter stretching the material to a final thickness less than 0.002 inches. The conventional manufacturing of films having thicknesses below 0.002 inches during pre-sinter expansion often result in breaking or tearing of the film.

Conventional methods of processing expanded polymers, such as PTFE (polytetrafluoroethylene), PET (polyethylene terephthalate), and UHMWPE (ultra high molecular weight polyethylene), require high temperatures and pressures as discussed. These high temperatures and pressures are not conducive to inclusion of a drug or active agent during the process of expansion. Such conditions have deleterious effects on the drugs and agents.

Therefore, a need exists for a method providing substantial expansion of expandable polymers, without need for heating, to create uniform material with alternate polymer morphologies. Furthermore, the ability to decrease thickness, increase strength, uniformity and density of expandable polymers is desirable in many applications. In addition, the ability to include a drug or otherwise active agent in the expandable polymer is desirable to enable the application of the drug or agent to targeted locations requiring treatment.

SUMMARY

The present invention is directed generally to methods for treating expandable polymers and products produced therefrom. More particularly, the invention relates to methods for forming an article from an expandable polymer that has been stretched involving the steps of rewetting the expandable polymer with a wettable liquid to form a wetted material, and stretching the wetted material. The wettable liquid can later be removed.

The wettable liquid can be formed at least partially with a drug or agent. The drug or agent intersperses throughout at least a portion of the expandable polymer during the wetting and/or re-wetting processes.

According to another aspect of the invention, an article is formed by rewetting an expandable polymer and then stretching the expandable polymer.

Expandable polymer articles formed in accordance with the processes of the invention have characteristics, such as uniformity, porosity, density, node size, thickness, fibril density and permeability not attainable from conventional methods.

The method of the present invention provides for an increased drug loading capacity relative to conventional drug incorporation methods, such as immersion and impregnation.

These and other features, aspects, and advantages of the present invention will become better understood with reference to the following description and appended claims.

BRIEF DESCRIPTION OF THE DRAWINGS

The subject matter regarded as the invention is particularly pointed out and distinctly claimed in the concluding portion of the specification. The invention, however, both as to organization and method of practice, together with further objects and advantages thereof, is best understood by reference to the following illustrative descriptions taken in conjunction with the accompanying drawings in which like numerals refer to like elements.

FIG. 31 illustrates a chart depicting Heparin amounts for different samples;

FIG. 32 illustrates a chart showing a dose response of SNAP;

FIG. 33 illustrates a chart depicting a release of Rapamycin over time; and

FIG. 34 illustrates an additional chart depicting Rapamycin release.

DETAILED DESCRIPTION

Figure 1A:
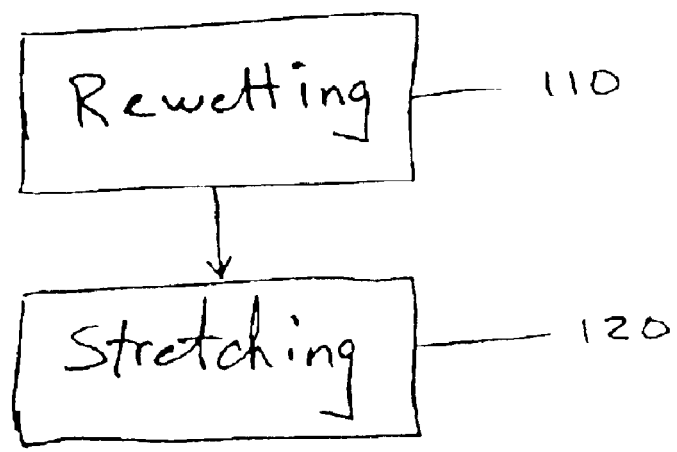
FIG. 1A illustrates an exemplary method of a first embodiment of the invention.

The present invention provides a means for expanding expandable polymers at or below room temperature without breakage and maintaining a substantially uniform material, and allows one to achieve a greater expansion ratio than that allowed at elevated temperatures using known methods. Furthermore, the present invention provides a method for inclusion of a drug or active agent in the composition of the expanded polymers. The expanded polymers can be formed into a plurality of different devices and utilized to apply the drug or active agent in a targeted and/or time extended manner. In addition, the method of the present invention provides for an increased drug loading capacity relative to conventional drug incorporation methods, such as immersion and impregnation.

Polymers with ordered microstructures, often referred to as highly crystalline, have the fundamental ability to expand into another shape and size. Fluoropolymers and polyolefins are polymers suitable for expansion processes. Fluoropolymers include homopolymers of polytetrafluoroethylene (PTFE), and copolymers of polytetrafluoroethylene in which the co-monomer is ethylene, chlorotrifluoroethylene, perfluoroalkoxytetrafluoroethylene, and fluorinated propylene. Polyolefins include polypropylene and polyethylene.

The concept of contact angle and its equilibrium is valuable because it can be used to define wettability. When a liquid wets a solid, it spreads freely over the surface at a rate depending on the liquid viscosity and surface tension, and solid surface roughness, porosity, and chemistry. The tendency for the liquid to spread increases as contact angle decreases so contact angle is a useful inverse measure of wettability. Contact angle is the angle measured which the liquid makes with a solid. The contact angle of a liquid is a result of the thermodynamic equilibrium of a drop on a solid surface. Solids, liquids, and gases, exist in equilibrium. At the interface between a liquid and solid, the interfacial monolayer of the liquid is attracted by the bulk liquid and gas from one side and from the other side by the intermolecular forces, which interact between the solid and liquid. A porous material is said to be "wet" when the voids of the material are at least partially occupied by a given fluid.

In accordance with the invention, multi-directional expansion of an expandable polymer (sintered or unsintered) can occur at room temperature provided the material is rewet with a wettable liquid before or during the expansion step. Rewetting involves the application of wettable liquid after completion of activities for which wettable liquid may be used, such as extrusion. Removal of any previous wettable liquid is not required before rewetting. This method is not limited to room temperature conditions and can be applied whenever the expandable polymer is rewet with the wettable liquid. Ideally, the expansion is performed at a temperature below the vaporization or boiling points of the wettable liquid.

Wet stretch is defined herein as the expansion or deformation of an expandable polymer in one or more directions when the material is wet with a wettable liquid before or during the expansion step. Wet stretching of an expandable polymer resin, such as PTFE, can provide: modified processability, material structures which differ from those made from conventionally processed resin, for example, decreased thickness, increased density, and product uniformity. The overall feel of the product is typically enhanced, due to increased smoothness.

Major differences can be seen in the structures according to the invention compared to conventionally processed material. The invention typically provides increased density and improved strength, allowing products to be thinner than those made from conventional methods.

The extrudate may also be sintered, after stretching or before stretching, by heating it to a temperature above its crystalline melting point while being maintained in a stretched condition. This can be considered an amorphous locking process for permanently "locking-in" the microstructure in the expanded or stretched configuration. The methods of the invention can simultaneously provide greatly reduced sintering times and improved product structure over conventional methods. The present invention does not require sintering for certain applications, including endovascular, filtration, and the like, as is typically required by conventional methods. In addition, sintering can only be utilized in combination with a drug or active agent if that drug or active agent is not compromised by the conditions of the sintering process.

The ability to increase the amount of expansion in either sintered or unsintered expandable polymers has a wide variety of applications in medical, industrial, and consumer products. For example: laminate structures with varying properties for filters and membranes; medical implants with tailored porosities to control body fluid leakage and tissue ingrowth; radially expandable PTFE with reduced expansion force and/or increased expansion ratios for endovascular applications.

A variety of forms and sizes are included in the scope of the invention. For example, flat sheets, hollow tubes, and solid rods, can be manufactured and utilized in many applications. Furthermore, the invention is applicable to any structures formable by conventional expandable polymer methods.

Expanded PTFE material is characterized by lengthwise-oriented fibrils interrupted by transverse nodes. The pore size in microns is typically determined by measuring fiber length between the nodes (internodal distance). To compute fibril length, the material is viewed under sufficient magnification. A fibril length is measured from one edge of one node to the edge of an adjacent node. Fibril lengths are measured from the sample to compute a mean fibril length.

Nodes and fibrils may be further characterized by their relative geometry. That is, nodes by length, width, and height; and fibrils, by diameter and length. It is the relative geometry of nodes to fibrils, as well as, internodal distance and fibril density that determines porosity and permeability of porous PTFE. The physical space between connecting nodes is composed of solid thread like PTFE fibers called fibrils in conjunction with a gaseous void volume. Fibril density refers to the relative volume consumed by fibrils between the nodes.

Permeability or hydraulic conductivity is related to material porosity. Permeability to fluid flow can be determined by measuring the amount of pressure required for water to permeate the pores of the material. Water entry pressure (WEP) is a good measuring technique to assess this trait because it closely mimics the permeation process at the liquid/solid interface. WEP is defined as the pressure value necessary to push water into the pores of a synthetic tubular substrate and can be classified as: High (>400 mm Hg), Medium (200-400 mm Hg), and Low (<200 mm Hg). To compute WEP, the material is subjected to an incrementally increasing water pressure until small beads of water appear on the surface.

Machine direction (MD) refers to the direction in which the polymeric material travels through the processing machine. Transverse direction (TD) refers to the direction that is perpendicular to the MD. Longitudinal Tensile Strength (LTS) is measured in pounds, per square inch by dividing the tensile force applied to the material by the cross-sectional area of the material. Radial Tensile Strength (RTS) is also measured in pounds per square inch. RTS is obtained by dividing the radial expansion force applied to the material by the cross-sectional area of the material. Cross-sectional area is the amount of material subjected to a controlled strain during tensile testing defined as the sample width multiplied by its thickness.

Suture Retention strength (SRT), measured in pounds, indicates the amount of force needed to pull out sutures from the polymeric material.

The invention will now be described with reference to exemplary embodiments. Cylinders, tubes, sheets, or other shapes can be created by either of these embodiments.

The embodiments involve the use of expandable polymers. Although expandable polymer material may be prepared in a variety of ways, one method involves the use of wettable liquid to aid an initial extrusion process. A wettable liquid is capable of entering the pores of the expandable polymer resin. The invention is not limited to expandable polymers prepared by extrusion, or by the use of a wettable liquid for extrusion.

By way of example, an expandable polymer resin, such as PTFE resin (Fluon CD-123 obtained from ICI Americas), may be blended with a first wettable liquid, such as ISOPAR-H odorless solvent (produced by EXXON Corporation), to form a lubricated powder. The wettable liquid can further include one or more drugs or agents desired to be incorporated into the expandable polymer. This results in the lubricated powder containing the one or more drugs or agents.

The wettable liquid may be mixed with the resin to control the degree of material shear that occurs during subsequent extrusion and to prevent excessive shear, which can damage the material. Again, the wettable liquid can include one or more drugs or agents for incorporation into the expandable polymer. By application of pressure, the lubricated powder may then be preformed into a billet, typically shaped like a large cylinder.

Alternatively, the resin may be mixed with a powder form of the one or more drugs or agents. The combination of the resin with the powder can occur before, during, or after the addition of the wettable liquid in forming the expandable polymer.

Using a ram-type extruder, the billet may be extruded through a die having a desired cross-section, typically a circle, thereby forming a cylinder. A variety of shapes may be formed by extrusion, such as a solid or hollow cylinder, a flat sheet, a rectangle and the like.

Figure 1B:
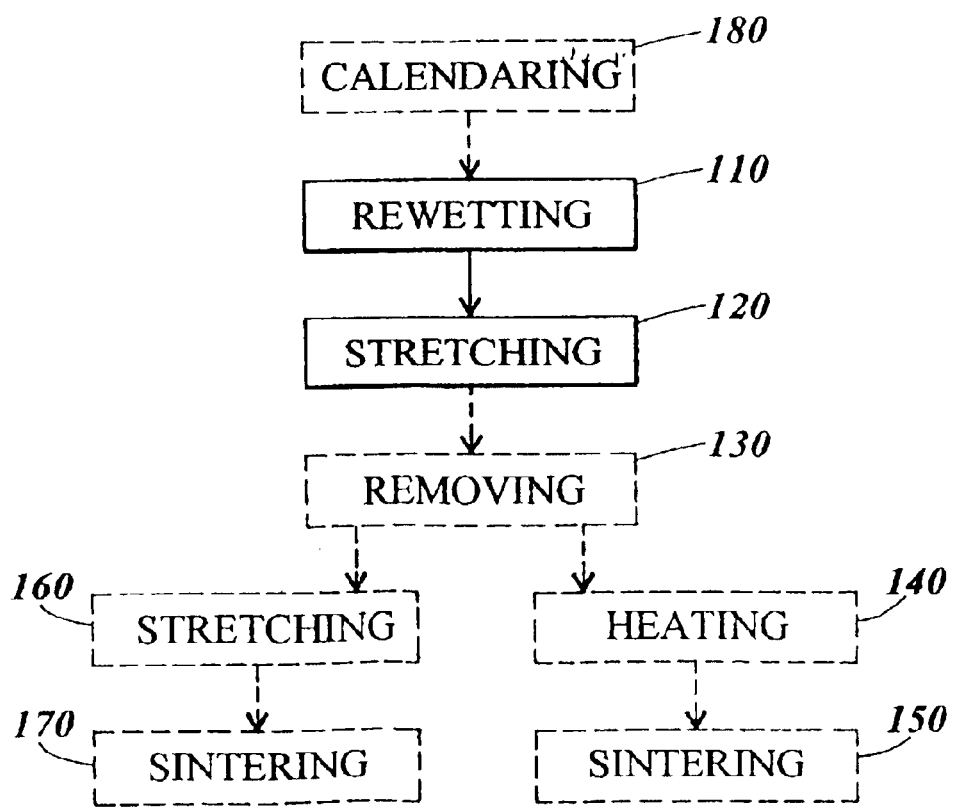
FIG. 1B illustrates exemplary variations of a first embodiment of the invention.
Figure 1C:
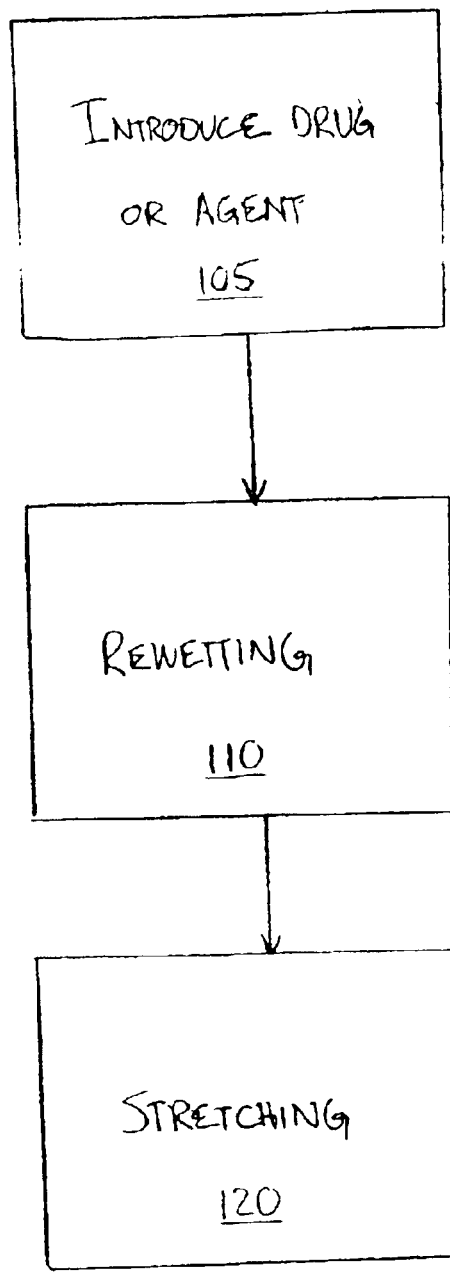
FIG. 1C illustrates exemplary variations of a first embodiment of the invention.

The first embodiment of the invention is described with reference to FIGS. 1A, 1B, and 1C. An expandable polymer is rewet, step 110, with a second wettable liquid such as ISOPAR-H. Rewetting may be performed by exposing the expandable polymer to the second wettable liquid, such as by submerging or soaking the expandable polymer in the second wettable liquid, spraying the second wettable liquid, or rubbing the second wettable liquid into the expandable polymer. As described above, rewetting involves the application of wettable liquid after completion of activities for which wettable liquid may be used, such as extrusion. Removal of any previous wettable liquid is not required before rewetting.

The one or more drugs or agents can be introduced (step 105) as discussed, in either of the first and second wettable liquids, or as a powder with the resin, if desired. The one or more drugs or agents can soak in and penetrate the expandable polymer during the manufacturing process.

Use of the second wettable liquid results in substantially uniform material with increased density and substantially altered node structure. Ideally, the second wettable liquid completely saturates the expandable polymer. As with all embodiments described herein, elevated temperature or pressure above ambient conditions may be used in conjunction with the application of a wettable liquid to reduce the time necessary for saturation or aid in saturation of the expandable polymer.

Stretching, step 120, is then performed, preferably at a temperature below a boiling point of the second wettable liquid. Stretching can be performed in more than one direction. Stretching is typically performed, in the case of a cylinder, by applying tensile force to the ends of the cylinder. In the case of a flat sheet, stretching is typically performed in the machine direction. Alternatively, or in addition, stretching may be performed in the radial or transverse direction to a cylinder or flat sheet, respectively. For example, in the case of a hollow cylinder, a mandrel may be used to radially stretch the hollow polymer cylinder. Tensile force may be applied to stretch the cylinder simultaneously with the use of a mandrel or at a different time. Within the scope of the invention, a combination of various stretching may be combined or applied in succession.

As with all embodiments described herein, heat may also be applied to the expandable polymer prior to or during stretching. It is preferable to keep the temperature of the expandable polymer below a boiling point of the second wettable liquid to inhibit loss of the second wettable liquid. It is further preferable to keep the temperature of the expandable polymer and the wettable liquids below a degradation point of any drugs or agents incorporated into the expandable polymer and wettable liquids.

Although ISOPAR-H is used as the first and second wettable liquids in this embodiment, other permeating liquids are within the scope of the invention and can be considered interchangeable with ISOPAR-H or other wettable liquids. As an example, polyethylene glycol is preferred for in vivo applications because it is a biocompatible liquid. Naphtha is another example of a wettable liquid that may be used within the scope of the invention. Poly lactic acid is a further possible wettable liquid. Alcohol and water may also be used in combination. It is also within the scope of the invention to use one wettable liquid during the initial extrusion process and another wettable liquid for rewetting. Also, the combination of liquids may be used during either extrusion or rewetting.

It should again be noted that the first and second wettable liquids can include the incorporation of drugs and/or agents. The conditions involved in the process of expansion are amenable to such inclusion. This introduces the opportunity to substitute hydrocarbon based aids, or other extrusion aids, with a plurality of wettable liquids, including alcohol-based and aqueous-based liquids.

One example liquid mentioned as suitable for inclusion in the expanded polymers is polyethylene glycol. The drug or agent, for example Heparin, can mix with the polyethylene glycol to produce the wettable liquid. The expanded polymer resulting from the use of the mixture for the wettable liquid will release Heparin in a controlled manner. The rate of release of the drug or agent can likewise be varied by altering the volumes, ratios, and contents of the mixtures. Other drugs or drug agents can be incorporated into the wettable liquid for use in accordance with the teachings of the present invention. Table 1 is provided below of some example drugs or agents suitable for use in accordance with the teachings of the present invention:

TABLE 1

| Class | Examples |
| --- | --- |
| Antioxidants | Lazaroid, Probucol, Vitamin E |
| Antihypertensive Agents | Diltiazem, Nifedipine, Verapamil |
| Antiinflammatory Agents | Glucocorticoids, Cyclosporine, NSAIDS |
| Growth Factor Antagonists | Angiopeptin, trapidil, suramin |
| Antiplatelet Agents | Aspirin, Dipyridamole, Ticlopidine, Clopidogrel, GP IIb/IIIa inhibitors, Abeximab |
| Anticoagulant Agents | Heparin (low molecular weight and unfractionated), Wafarin, Hirudin |
| Thrombolytic Agents | Alteplase, Reteplase, Streptase, Urokinase, TPA |
| Drugs to Alter Lipid Metabolism (e.g. statins) | Fluvastatin, Colestipol, Lovastatin |
| ACE Inhibitors | Elanapril, Fosinopril, Cilazapril |
| Antihypertensive Agents | Prazosin, Doxazosin |
| Antiproliferatives and Antineoplastics | Cochicine, mitomycin C, Rapamycin, taxols, Everolimus, Tacrolimus, Sirolimus |
| Tissue growth stimulants | Bone morphogeneic protein, fibroblast growth factor |
| Gasses | Nitric oxide, Super Oxygenated $O_2$ |
| Promotion of hollow organ occlusion or thrombosis | Alcohol, Surgical Sealant Polymers, Polyvinyl particulates, 2-Octyl Cyanoacrylate, Hydrogels, Collagen |
| Functional Protein/Factor Delivery | Insulin, Human Growth Hormone, Estrogen, Nitric Oxide |
| Second messenger targeting | Protein kinase inhibitors |
| Angiogenic | Angiopoetin, VEGF |
| Anti-Angiogenic | Endostatin |
| Inhibition of Protein Synthesis | Halofuginone |
| Antiinfective Agents | Penicillin, gentamycin |
| Gene Delivery | Genes for Nitric Oxide Synthase, human growth hormone, antisense oligonucleotides |
| Local Tissue Perfusion | Alcohol, $H_2O$, Saline, Hot or Cold $H_2O$ for thermal ablation |
| Nitric Oxide Donating Derivatives | NCX 4016 - Nitric Oxide donating derivative of Aspirin |
| Contrast Media | |

The use of such wettable liquids make it possible for the delivery matrix to serve as the lubricant/extrusion aid during mixing, extrusion, and/or expansion.

Optionally, further steps of the preferred embodiment of the invention may include removing the second wettable liquid, step 130. Although removal can be accomplished at room temperature, heating to an elevated temperature accelerates removal of the second wettable liquid. However, heating may not be possible to the extent otherwise allowable with non-drug and non-agent liquids if the first and/or second wettable liquids instead include drugs or agents that are susceptible to heat, in which case an alternate method may be used such as extraction with a more volatile solvent.

Optional heating, step 140, to, for example, 320° C., can be performed following removal of the second wettable liquid, step 130. Heating, step 140, may optionally be sufficient to cause sintering, typically at about 360° C., thereby locking in the microstructure. Alternatively, sintering, step 150, may be conducted after heating.

A further alternative of the first embodiment involves a second stretching step 160, after optional removing of the wettable liquid, step 130. As discussed above, this second stretching step 160 may involve heating prior to or during stretching and may be conducted in the machine direction, a transverse direction, or any combination or sequential application thereof. Sintering, step 170, may optionally be performed after the second stretching.

A further variation of the first embodiment of the invention includes calendaring, step 180, before the rewetting step 110. Calendaring can be performed during the creation of flat sheets after extrusion of the expandable polymer. Preferably, calendaring rolls are operated at an elevated temperature, such as, for example, 130° F. However, one of ordinary skill in the art will appreciate that calendaring can be performed for other extruded shapes, if desired.

Figure 2A:
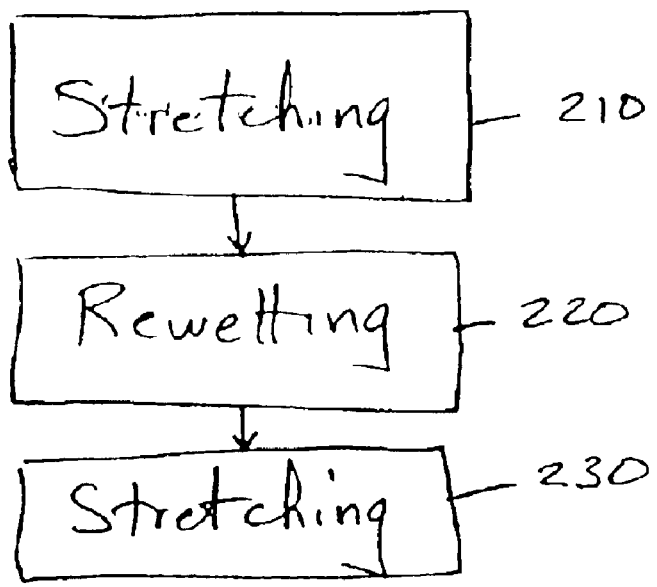
FIG. 2A illustrates an exemplary method of a second embodiment of the invention.
Figure 2B:
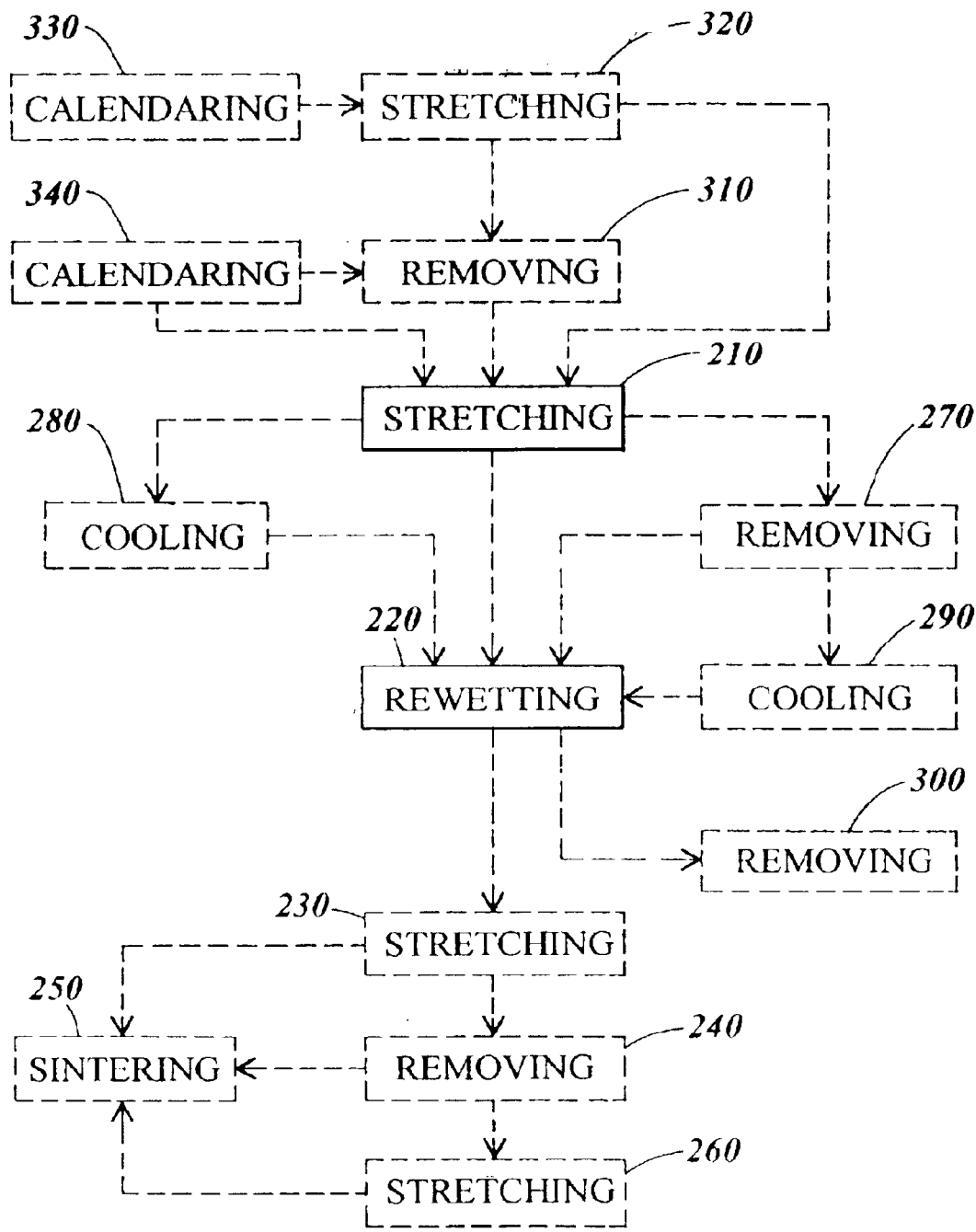
FIG. 2B illustrates exemplary variations of a second embodiment of the invention.
Figure 2C:
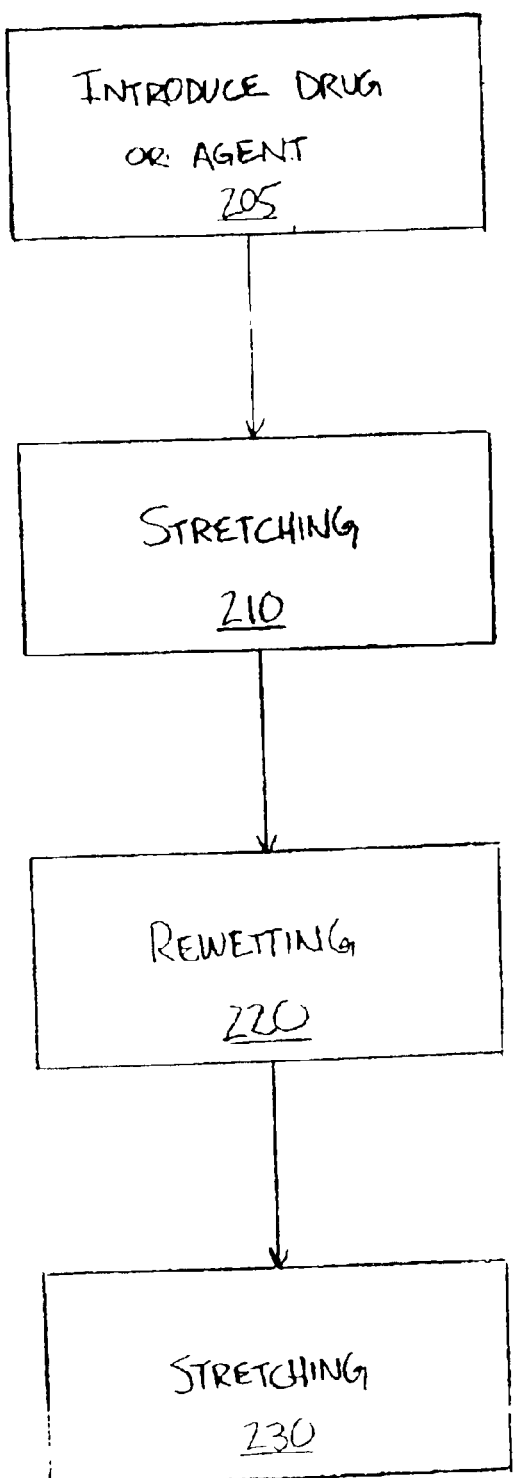
FIG. 2C illustrates exemplary variations of a second embodiment of the invention.

A second, embodiment of the invention is shown in FIGS. 2A, 2B, and 2C. The second embodiment of the invention differs from the first embodiment, at least in part, by stretching of the expandable polymer before rewetting with a second wettable liquid.

According to an exemplary method of the second embodiment, an expandable polymer is stretched, step 210. Because a second wettable liquid has not been applied, it is preferable that stretching be performed with heat, for example in radiant heat oven set to approximately 705° F., thereby allowing greater stretch ratios. Rewetting, step 220, is then performed by applying a second wettable liquid to the expandable polymer. As discussed in relation to rewetting step 110 of the first embodiment, a wettable liquid may be applied to the expandable polymer in a variety of ways. In addition, the wettable liquids applied can incorporate one or more drugs or agents in one or both of the first and second wettable liquids (step 205). For example, because this embodiment makes use of a heating step during stretching, it may be preferable to introduce the drug or agent with the second wettable liquid used during the expansion step. This would avoid the higher temperatures of the heating step, and thus avoid degradation of a drug or agent within the wettable liquid. If the drug or agent in the wettable liquid could withstand the heating step, the drug or agent can be included in that step as well.

Stretching, step 230, is performed as discussed in relation to the stretching step 120 of the first embodiment. Variations, including for example, heating and direction of stretching, discussed in relation to stretching step 120 of the first embodiment are also applicable to stretching step 230 of the second embodiment.

One variation of the second embodiment of the invention involves increased tension on a take-up roller during processing. This will provide a variation in properties of the resulting expandable polymer. Increased tension of the take-up roller will impart some longitudinal orientation to the nodes of the expandable polymer and create a thicker, less dense product than is typical without increased tension on the take-up roller.

Another variation of the second embodiment involves substituting the step of stretching 230 with the application of pressure sufficient to change the structure of the expandable polymer. By way of example, pressure may be applied by the use of rollers to crush the expandable polymer.

The second embodiment of the invention may also include removal of the second wettable liquid from the expandable polymer. Removal of the second wettable liquid, step 240, is optionally performed after the stretching step 230. Further optional variations include single or multi-directional stretching as discussed above in relation to the stretching step 120 of the first embodiment, or sintering, step 250, after removal of the second wettable liquid, step 240.

Alternatively, a third stretching step 260 may be performed after removal of the second wettable liquid, step 240.

A further variation of the second embodiment involves sintering, step 250, after the second stretching step 230, or the removal of the second wettable liquid, step 240, or stretching step 260.

Another variation of the second embodiment includes removal of the first wettable liquid, step 270, after the stretching step 210. According to another variation, cooling, step 280, may be performed prior to the rewetting step 220. Cooling, step 290, may also be performed after optional removal of the first wettable liquid, step 270.

A further variation of the second embodiment includes removal of the second wettable liquid, step 300, after the rewetting step 220. In this variation, the second stretching step 230 is not conducted.

The second embodiment may also include the application of heat during the first stretching step 210. The step of stretching without heat or use of a wettable liquid typically cannot involve high stretch ratios without risk of tearing the expandable polymer.

Further variations of the second embodiment include removal of the first wettable liquid, step 310, prior to the first stretching step 210. Another variation includes preliminary stretching of the expandable polymer, step 320, before the first stretching step 210. Preliminary stretching, step 320, before the first stretching step 210 may be conducted prior to optional removal of the first wettable liquid, step 310, but the invention is not so limited and stretching may be conducted without removal of the first wettable liquid.

A further variation of the second embodiment includes calendaring. As discussed in relation to the first embodiment, calendaring is typically performed during the creation of a flat sheet. The step of calendaring 330, 340 may be conducted shortly after extrusion of the expandable polymer, such as before the step of preliminary stretching 310, the step of removal of the first wettable liquid 310, or stretching step 210.

The second embodiment can likewise include drugs or agents in one or both of the first and second wettable liquids. However, the optional steps of heating and sintering could require modification or may not be possible depending on the particular drug or agent liquid utilized.

The embodiments and their variations described above are intended to be representative of the scope of the invention and not limiting. It is also intended to be within the scope of the invention for variations of the embodiments to be applicable to other embodiments. For example, variations of the second embodiment may be used in combination with methods of the first embodiment.

The invention will now be described with respect to various examples involving various forms, beginning with sheets and films.

EXAMPLE #1

Example 1 of the invention, Material D, involves flat material that is stretched in the machine direction according to the second embodiment of the invention. This example provides increased density of the material and an altered node structure from those available by conventional methods.

PTFE resin (Fluon CD-123 obtained from ICI Americas) was blended with ISOPAR-H odorless lubricant solvent (produced by EXXON Corporation) at a level of 19.5% by weight to form a lubricated powder. The lubricated powder was then compressed into a cylinder and ram extruded into a flat sheet 6 inches across and 0.040 inches thick. The flat sheet was then compressed through two heated rolls to form a film having a thickness of 5 mil. The lubricant was then removed from the film by passing the film through a radiant heat oven set to 490° F. to drive off the ISOPAR-H.

Figure 3:
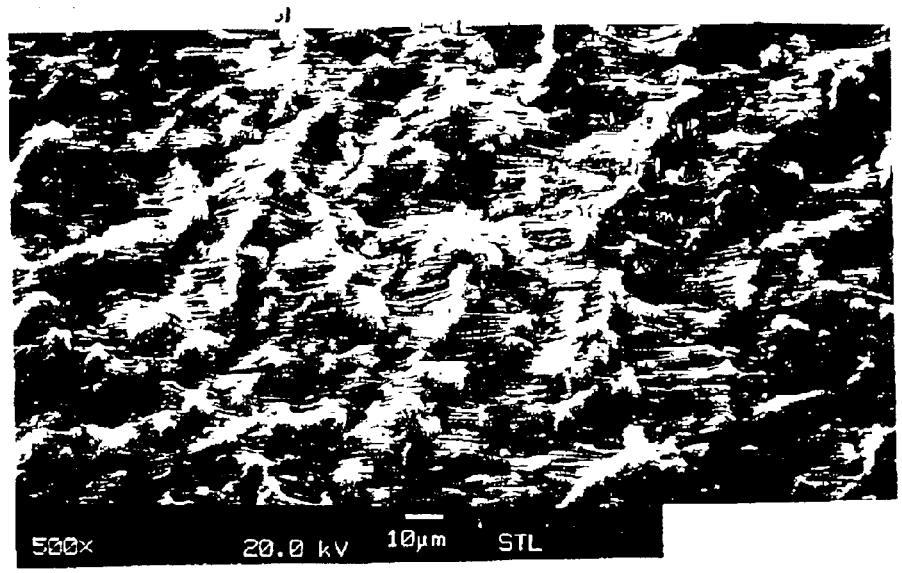
FIG. 3 provides a scanning electron micrograph (SEM) of Material A.

The film was then stretched in the machine direction at a ratio of 10:1 in a radiant oven set at 705° F. to form a Material A. A scanning electron micrograph (SEM) of Material A is shown in FIG. 3. A control experiment was performed where Material A was restretched in the machine direction at a ratio of 1.8:1 with the use of heat but with no wettable liquid to form a Material B shown in FIG. 4. A further experiment was performed to stretch Material A to a ratio of 1.8:1 in the machine direction without the use of heat or wettable liquid to attempt to form a Material C. However, the sample broke before reaching the ratio of 1.8:1. Materials A and B represent samples prepared according to conventional methods. The attempt to form Material C demonstrates the need for heat in conventional stretching methods.

Figure 5:
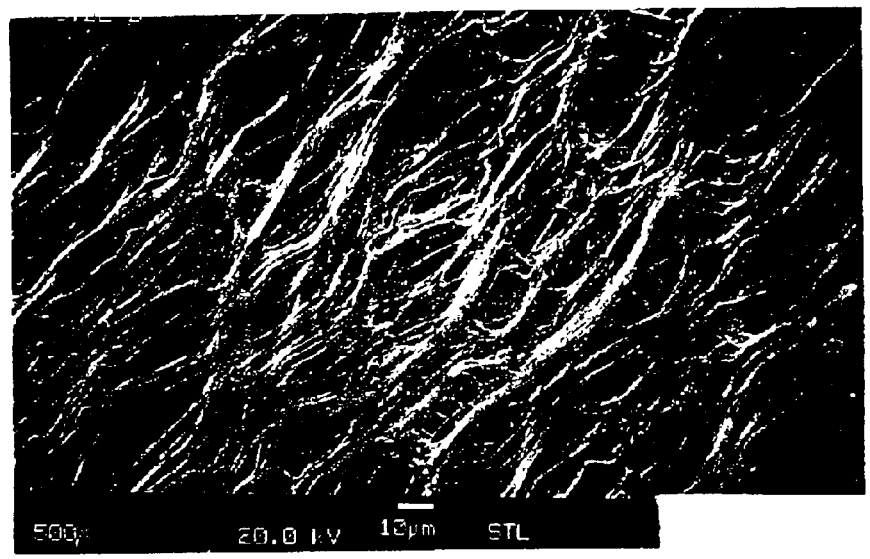
FIG. 5 provides an SEM of Material D of the invention.

According to Example 1 of the invention, Material A is rewet with the ISOPAR-H wettable liquid and stretched in the machine direction at a ratio of 1.8:1 at room temperature to form a Material D. FIG. 5 shows the elongated nodes and alignment of the fibrils of Material D.

As summarized in Table 2, the film produced by Example 1, Material D, is thinner and has a higher density than a similarly-stretched film produced by a conventional method, Material B. The node structure that is obtained by these two methods differs drastically, as shown in FIGS. 4 and 5.

Figure 4:
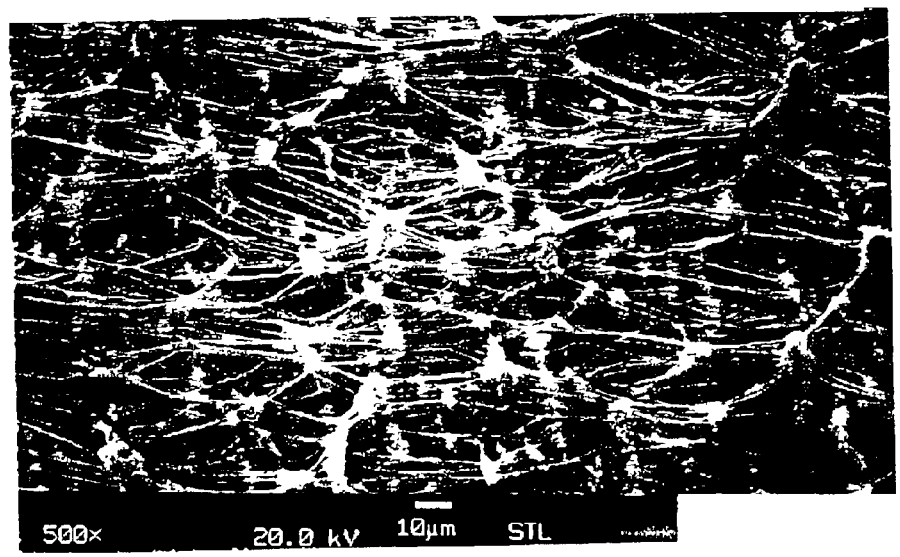
FIG. 4 provides an SEM of Material B.

FIGS. 4 and 5 illustrate that by stretching the material wet, a substantially different node structure is obtained than when conventional methods are used. Material B, shown in FIG. 4, is formed conventionally without wettable liquid and with heat and has a structure where the nodes are connected by fibrils that have a substantial amount of open space between them. Material D, shown in FIG. 5, the film formed by the method of Example 1 involving wettable liquid and no heat, consists of densely packed fibrils and drawn out nodes. As shown in Table 2, a lower thickness and a higher density are obtainable by using the method of Example 1.

embodiment of the invention to provide a thin, dense uniform material that has a low porosity. The same lubricated powder of Example 1 is compressed into a cylinder and ram extruded into a flat sheet 6 inches across and 0.040 inches thick. The flat sheet is then compressed through two heated rolls to form a film having a thickness of 10 ml, twice the thickness of the film of Example 1. The ISOPAR-H is then driven off by passing the film through a radiant oven set to 490° F. The film is then stretched in the machine direction, in a radiant oven set at 705° F. at a ratio of 6:1 to form a Material E.

Two control experiments were performed at the same transverse stretch ratio. A first control sample, Material F, was created with heat and no wettable liquid; the other sample, Material G, was created at room temperature also with no wettable liquid.

Figure 6:
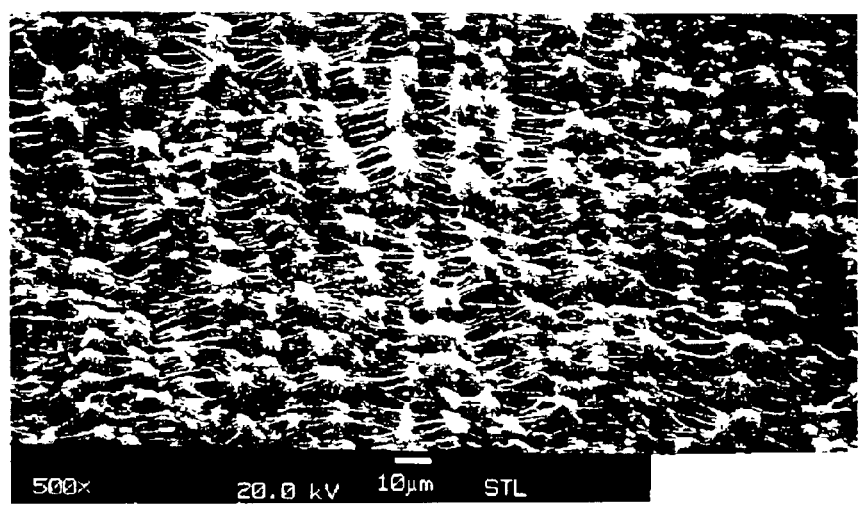
FIG. 6 provides an SEM of Material F.

Material F was made by stretching Material E in the transverse direction, with heat to a 12:1 stretch ratio. Material F has a star-like structure. FIG. 6 shows a scanning electron micrograph (SEM) of Material F. Material F has a very inconsistent thickness that ranged from 4.3 mil in the center to 1 mil at the edges. The average density of this material is 0.319 g/cm$^3$.

Figure 7:
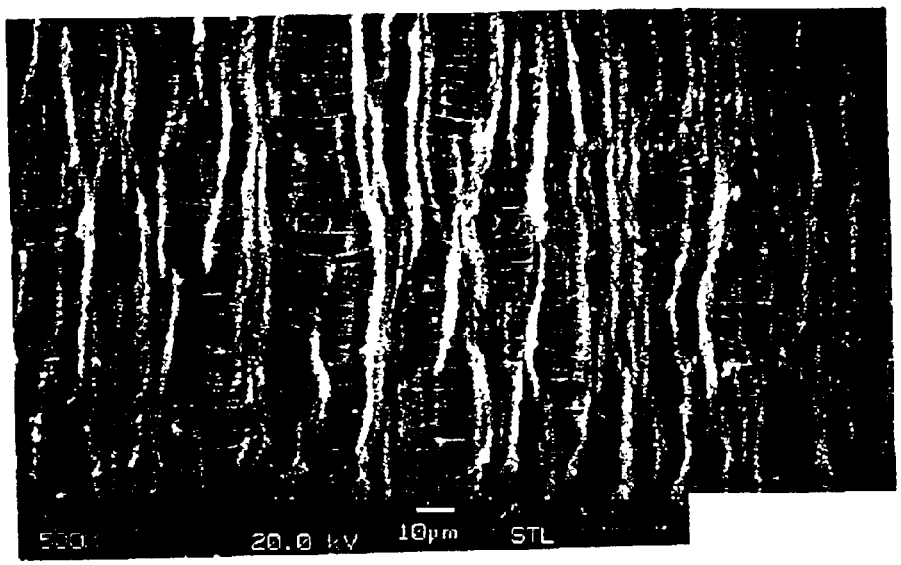
FIG. 7 provides an SEM of Material G.

Material G, another control sample, was made like Material F, except that stretching to a 12:1 ratio was performed at room temperature. A scanning electron micrograph (SEM) of Material G, is shown in FIG. 7. Material G has long ordered nodes with an internodal distance of about 15–30 microns. The density of Material G is 0.348 g/cm$^3$, similar to the other control, Material F.

Figure 8:
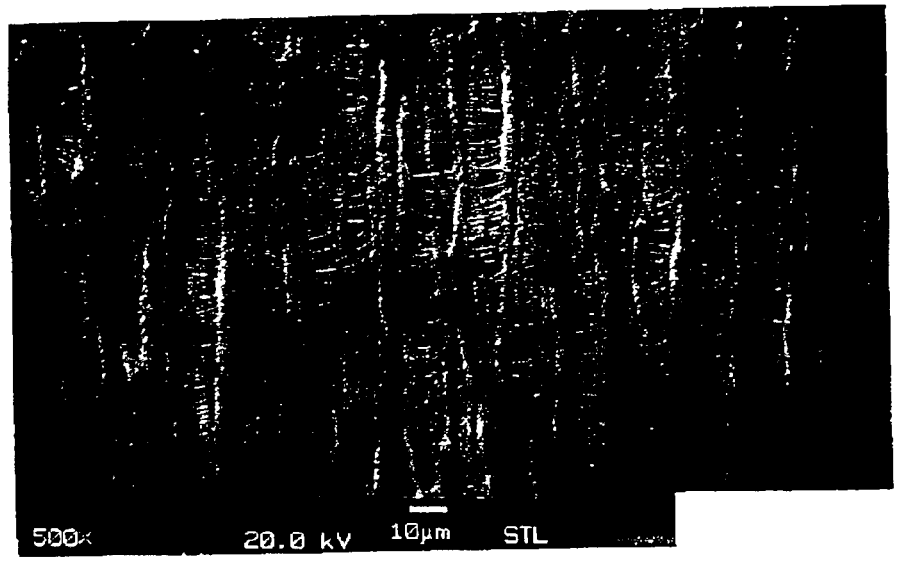
FIG. 8 provides an SEM of Material H of the invention.

According to one variation of the invention, Material E is wet with the ISOPAR-H wettable liquid and stretched in the transverse direction at a ratio of 12:1 at room temperature to form a Material H. FIG. 8 is a scanning electron micrograph of Material H. Material H has a node structure that has long drawn out nodes and very small internodal distances between and including 0 to 10 microns. The thickness of material H is consistently 0.5 mils, and the density of Material H is 1.228 g/cm$^3$, which is approximately four times higher than control materials, Materials F and G.

Figure 9:
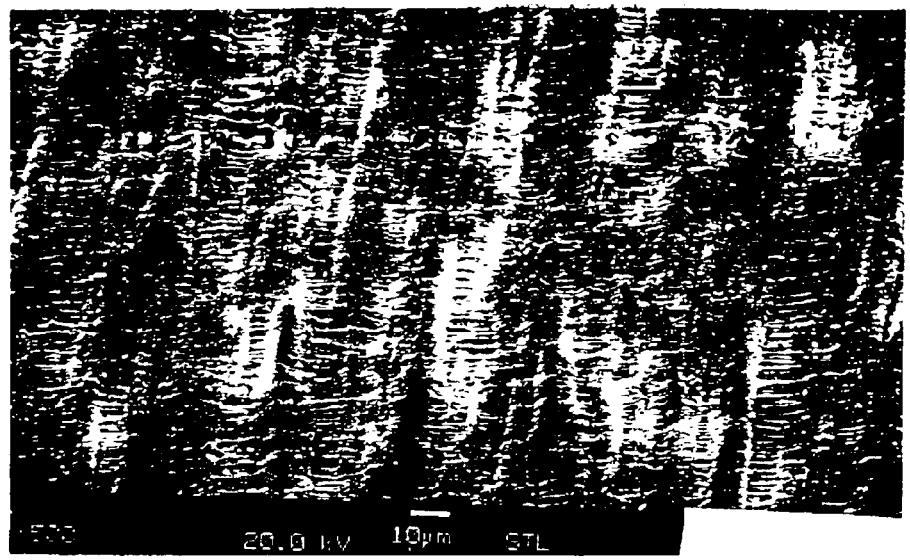
FIG. 9 provides an SEM of Material I of the invention.

Material I, shown in FIG. 9, is material that started out as Material H. The wettable liquid was then removed and the material was stretched a second time. This second stretch was in the transverse direction with heat at a ratio of 2:1.

Another variation of the invention, Material J, involves increasing tension on the take-up roller to stretch the material in the machine direction during stretching in the transverse direction. Material J is very similar to Material H involving wetting Material E with wettable liquid prior to transverse stretching at room temperature. Increased tension

TABLE 2

| Mat'l. | First MD Ratio | Wet/ Dry | Hot/ Cold | Second MD Ratio | Thickness Mil | Density (g/cm$^3$) | Machine Direction | | | | Transverse Direction | | | |
|---|---|---|---|---|---|---|---|---|---|---|---|---|---|---|
| | | | | | | | LTS (lbf) | LTS (psi) | Elong (in) | Elong (%) | LTS (lbf) | LTS (psi) | Elong (in) | Elong (%) |
| A | 10:1 | Dry | | 1:1 | 1.8 | 0.629 | 11.98 | 6656 | 0.75 | 50 | 0.05 | 27.8 | 23 | 1533 |
| B | 10:1 | Dry | Hot | 1.83.1 | 1.7 | 0.416 | 6.55 | 3853 | 0.4 | 26 6 | 0.03 | 15.7 | 22 | 1467 |
| C | 10:1 | Dry | Cold | 1.83:1 | Broke | | | | | | | | | |
| D | 10:1 | Wet | Cold | 1.83:1 | 1.3 | 0.954 | 3.25 | 2503 | 0.25 | 25 | 0.04 | 26.9 | 26 | 2600 |

EXAMPLE #2

Figure 10:
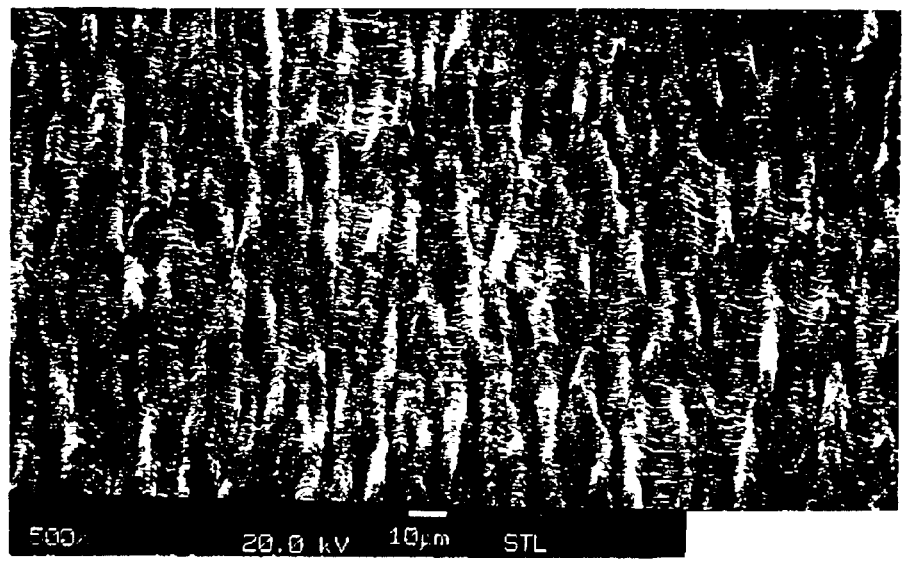
FIG. 10 provides an SEM of Material J of the invention.

Example 2 of the invention involves a flat material that is stretched in the transverse direction according to the second on the take up roller imparts some longitudinal orientation to the nodes. Material J was slightly thicker than Material H, 0.63 mils vs. 0.5 mils, and slightly less dense, 1.158 g/cm$^3$ vs. 1.228 g/cm³. As shown in FIG. 10, Material J has long wavy nodes and was very consistent across the material.

Materials H and J were stretched with the wettable liquid and were much more consistent in thickness and node structure than the two control samples, Materials F and G. The node structure and internodal distance of the materials were also drastically different. Materials H and J, processed by the inventive method, had a density four times higher and were significantly thinner with a different overall feel, than Materials F and G that were processed conventionally.

consistent at all ratios tested and it did not rip. The control material was not consistent and it had a tendency to rip. The overall look and feel of the materials was drastically different. The dry processed material had a tendency to shrink and had noticeable striations in it.

The present invention is applicable to a wide variety of product configurations. The following examples illustrate various embodiments of the invention involving tubes.

EXAMPLE #4

Example 4 involves longitudinal stretching of a tube according to the first embodiment of the invention. PTFE

TABLE 3

| Mat'l. | MD Ratio | TD Ratio | Hot/Cold | Wet/Dry | Thickness Mil | Density (g/cm³) | Machine Direction LTS (lbf) | LTS (psi) | Elong (in) | Elong (%) | Transverse Direction LTS (lbf) | LTS (psi) | Elong (in) | Elong (%) |
|---|---|---|---|---|---|---|---|---|---|---|---|---|---|---|
| F | 6:1 | 12:1 | Hot | Dry | 4.30 | 0.319 | 2.6 | 605 | 0.7 | 49 | 0.26 | 60.4 | 13 | 867 |
| G | 6:1 | 12:1 | Cold | Dry | 1.87 | 0.348 | 1.93 | 1032 | 1.3 | 89 | 0.34 | 182 | 6.5 | 433 |
| H | 6:1 | 12:1 | Cold | Wet | 0.50 | 1.228 | 2.86 | 5720 | 1.5 | 100 | 0.35 | 431 | 4.25 | 425 |
| I | 6:1 | 1) 12:1; 2) 2:1 | 1) Cold; 2) Hot | 1) Wet; 2) Dry | 1.10 | 0.877 | 2.52 | 4582 | 0.8 | 53 | — | — | — | — |
| J | 6:1 | 12:1 + MD tension | Cold | Wet | 0.63 | 1.158 | 3.62 | 5746 | 1.3 | 87 | 0.43 | 683 | 5.7 | 380 |

EXAMPLE #3

Example 3 of the invention involves a flat material that is stretched in the transverse direction according to the second embodiment of the invention to provide a thin, dense uniform material that has a low porosity. The same lubricated powder of Example 1 is compressed into a cylinder and ram extruded into a flat sheet 6 inches across and 0.040 inches thick. The flat sheet is then compressed through two heated rolls to form a film having a thickness of 5 mil. A first wettable liquid was then removed by passing the film through an oven. The film was then stretched in the machine direction at an elevated temperature to a ratio of 6:1. The control sample, labeled as Dry in Table 4, was then stretched in the transverse direction to the given ratio. This transverse stretching was done at room temperature at a line speed of 5 feet per minute. A sample according to the invention, labeled Wet in Table 4, was first soaked in a second wettable liquid and then stretched to the same transverse stretch ratios as the control sample.

TABLE 4

| | Thickness (Inches) | | Density (g/cm³) | |
|---|---|---|---|---|
| Ratio | Wet | Dry | Wet | Dry |
| 2:1 | .0030 | .0040 | 1.742 | 0.348 |
| 3:1 | .0028 | .0035 | 1.767 | 0.339 |
| 4:1 | .0025 | .0030 | 1.189 | 0.298 |
| 5:1 | .0020 | .0028 | 0.828 | 0.393 |
| 6:1 | .0015 | .0025 | 0.997 | 0.246 |
| 7:1 | .0004 | .0035 | 0.920 | 0.390 |
| 8:1 | .0005 | .0020 | 1.028 | 0.336 |
| 9:1 | .0003 | .0015 | 1.644 | 0.288 |

The thickness of the sample according to the invention was less than the control sample at every stretch ratio. The density of the inventive sample was found to be much higher than the control. The sample according to the invention was resin, Fluon CD-123, was blended with ISOPAR-H odorless solvent at a level of 17% by weight. The lubricated powder was then compressed into a cylinder and ram extruded into a 6 mm-diameter tube. The tube was then soaked in wettable liquid, ISOPAR-H, and stretched longitudinally at room temperature. The tube could easily be stretched to a ratio of 3:1. However, an attempt to stretch the 6 mm-diameter tube at room temperature to a ratio of 3:1 without wettable liquid resulted in the tube breaking.

EXAMPLE #5

Example 5 involves stretching of tubes both radially and longitudinally according to the second embodiment of the invention. A benefit of this example is a very thin, high density tube with a small internodal distance. As in Example 4, PTFE resin, Fluon CD-123, is blended with ISOPAR-H odorless solvent at a level of 17% by weight. The lubricated powder is then compressed into a cylinder and ram extruded into a 2 mm-diameter tube. The ISOPAR-H is driven off in a convection oven at 250° F. The tube is then expanded longitudinally at a rate of 5 inches/sec in a convection oven at a temperature of 320° C.

Figure 11:
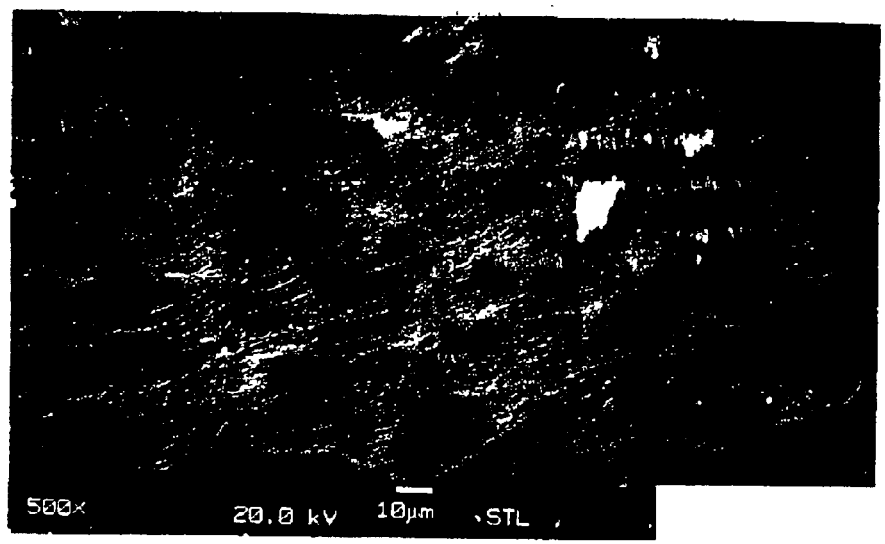
FIG. 11 provides an SEM of Material K of the invention.

The tube is then rewet with ISOPAR-H and stretched over a 19 mm mandrel. The ISOPAR-H is driven off in a convection oven at 250° F. The tube is then sintered in a convection oven at 360° C. The resulting tube, Material K shown in FIG. 11, has a thickness of 0.5 mil and has an inner porosity of <1 μm. The density of Material K is approximately 1.25 g/cm³.

Radial expansion over the 19 mm mandrel is not possible without the addition of the wettable liquid. An attempt to put a non-sintered tube over the same mandrel when it was not wet with wettable liquid resulted in a longitudinal split of the tube.

EXAMPLE #6

This example involves changing the node structure and density of an ePTFE tube by stretching it longitudinally while it was wet with wettable liquid. As in Example 4, PTFE resin, Fluon CD-123, is blended with ISOPAR-H odorless solvent at a level of 17% by weight. The lubricated powder is then compressed into a cylinder and ram extruded into a 6 mm-diameter tube.

Figure 12:
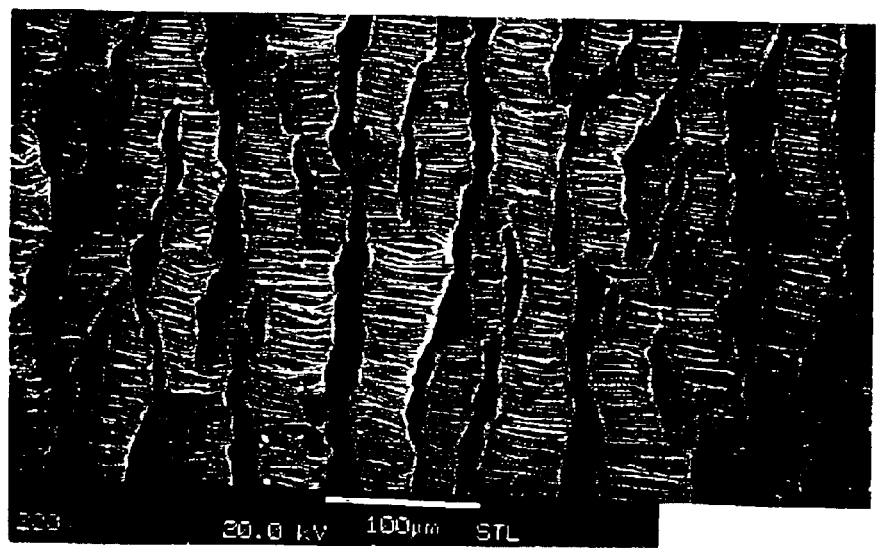
FIG. 12 provides an SEM of Material L.
Figure 13:
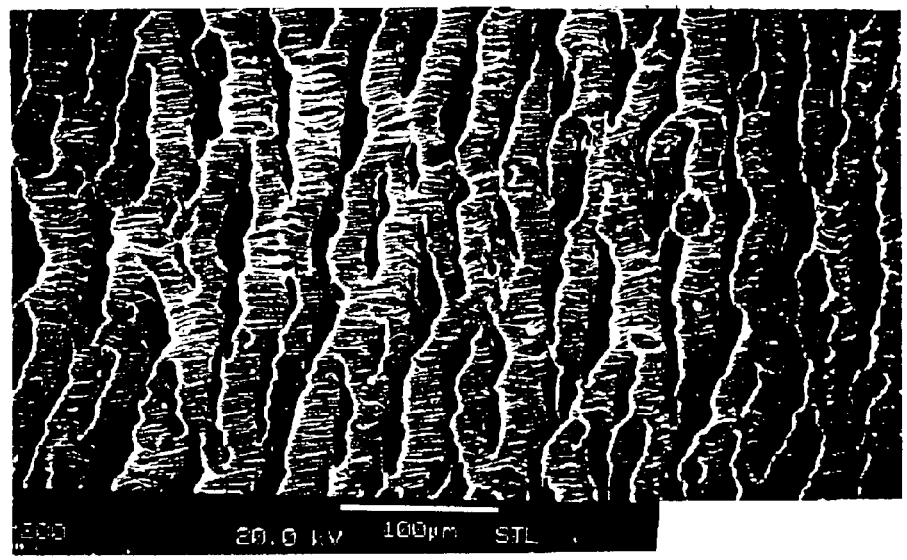
FIG. 13 provides an SEM of Material M.

Two control samples were prepared according to conventional methods using the above extrudate. Material L, shown in FIG. 12, was formed by stretching from 15"–45" with heat and then sintering. Material M, shown in FIG. 13, was formed by stretching from 15" to 30" with heat and then stretching from 30"–45" at room temperature, without the use of wettable liquid, followed by sintering.

Figure 14:
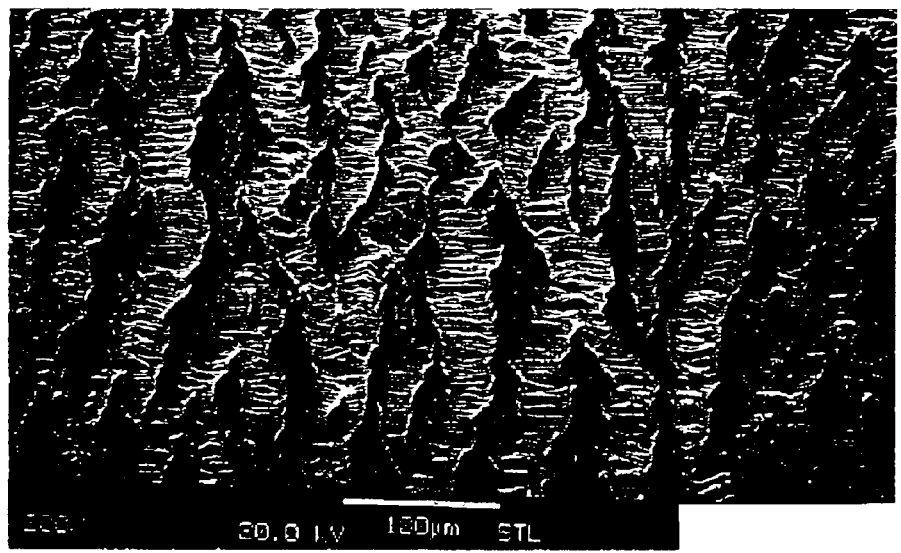
FIG. 14 provides an SEM of Material N of the invention.
Figure 15:
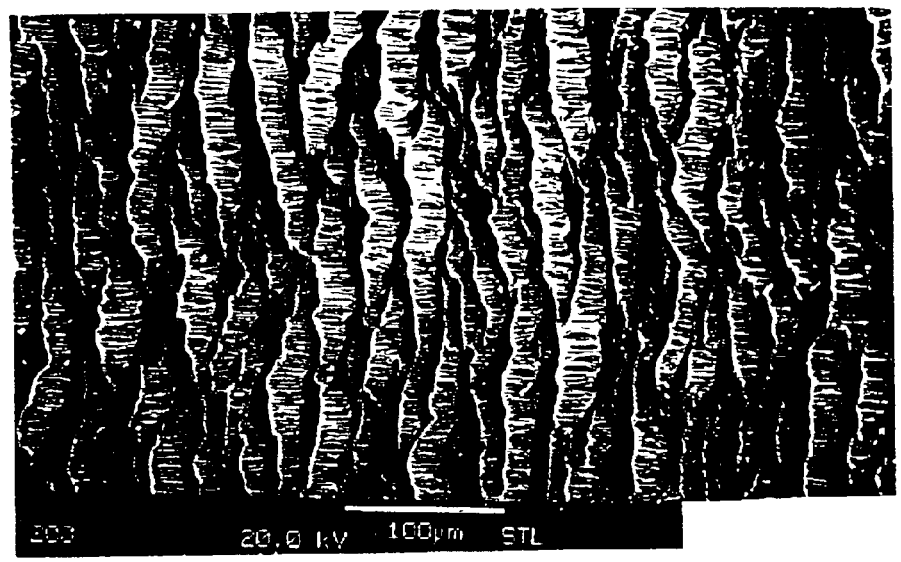
FIG. 15 provides an SEM of Material O of the invention.

Material N, shown in FIG. 14, was formed in accordance with the second embodiment of the invention by first stretching from 15"–30" with heat. It was then wet with the wettable liquid and stretched from 30"–45" at room temperature. The wettable liquid was then removed and sintering was performed to create Material N. Material O, shown in FIG. 15, was created in accordance with the first embodiment of the invention by wetting with a wettable liquid, then stretching from 15"–20" at room temperature. The wettable liquid was then removed and stretching with heat longitudinally to 45" was performed, followed by sintering.

Material N has a lower internodal distance than the conventional sample Material L. When compared to Material N, Material M was found to have approximately the same internodal distance but with smaller nodes. Material O has a very tight internodal distance and very small nodes when compared to the conventional sample, Material L. All three samples have a higher water entry pressure than the control with Material O being the highest. The only other mechanical property that was changed was suture retention strength, see Table 5.

TABLE 5

| Mat'l | LTS (lbf) | RTS (lbf) | SRT (lbf) | WEP (psi) | ID (in) | Wall Thickness (in) | Density g/cm³ |
|---|---|---|---|---|---|---|---|
| L | 48.36 | 17 | 0.27 | 227 | 0.234 | 0.014 | 0.712 |
| M | 46.06 | 17 | 0.23 | 312 | 0.234 | 0.015 | 0.634 |
| N | 42.70 | 17 | 0.19 | 300 | 0.236 | 0.016 | 0.596 |
| O | 46.46 | 20 | 0.22 | >365 | 0.220 | 0.013 | 0.912 |

EXAMPLE #7

A further example of the invention involves a tube comprised of layers with varying porosity. Variation in porosity can allow enhanced blood flow through a vascular graft, while still enabling tissue to grow into the external surface of the graft. It can also provide for selective filtration through the various pore size layers. Vascular grafts prepared in a layered fashion consist of a highly stretched inner layer mounted on a 6 mm mandrel that is wrapped with a tight porosity ePTFE film and covered with a high porosity outer layer. The resulting tube has a smooth, silky feel with a 10 mil wall thickness. By use of the second embodiment of the present invention, the node structure of one or more of the layers of the tube can be altered.

Figure 16:
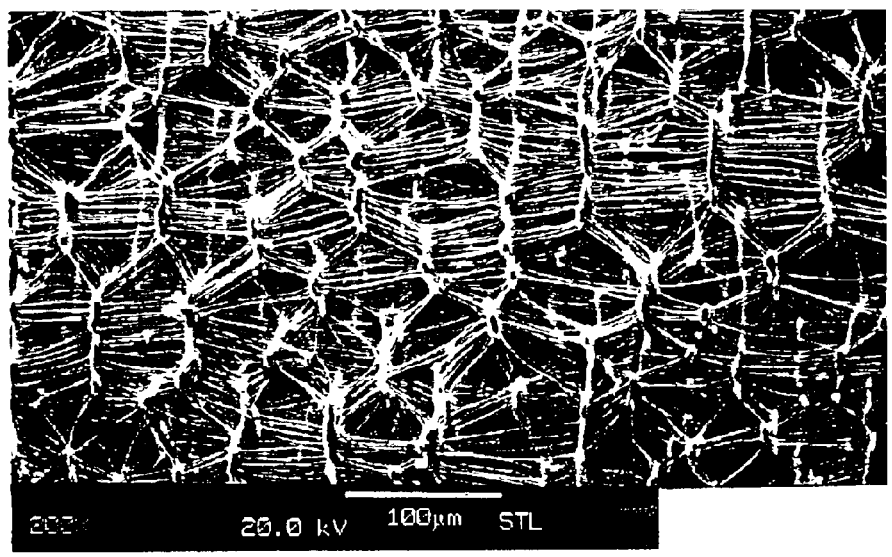
FIG. 16 provides an SEM of an exterior of Sample P.
Figure 17:
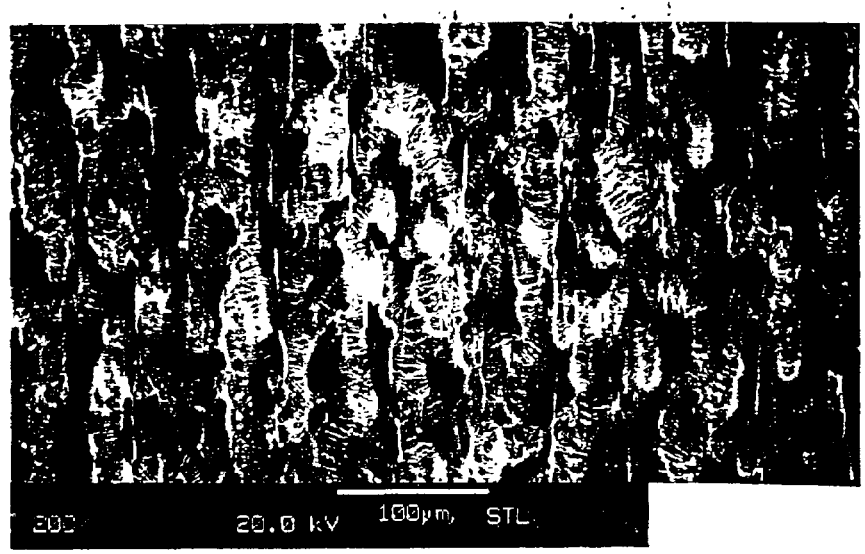
FIG. 17 provides an SEM of an interior of Sample P.
Figure 18:
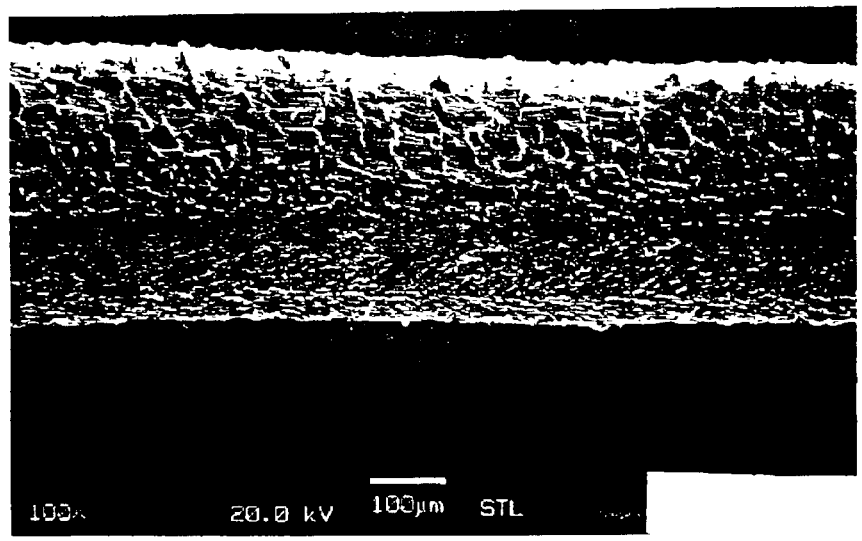
FIG. 18 provides an SEM of a cross-section of Sample P.

Sample P, shown in FIGS. 16–18, is an example of a vascular graft prepared according to steps described in U.S. Pat. No. 5,824,050, incorporated by reference herein. A highly stretched and sintered graft is placed onto a mandrel where it is wrapped, covered with a sintered cover and sintered together. FIG. 16 illustrates the structure of an exterior surface, and FIG. 17 illustrates an interior surface. FIG. 18 provides a cross-sectional view, showing the changing structure along the radius of the graft.

Figure 19:
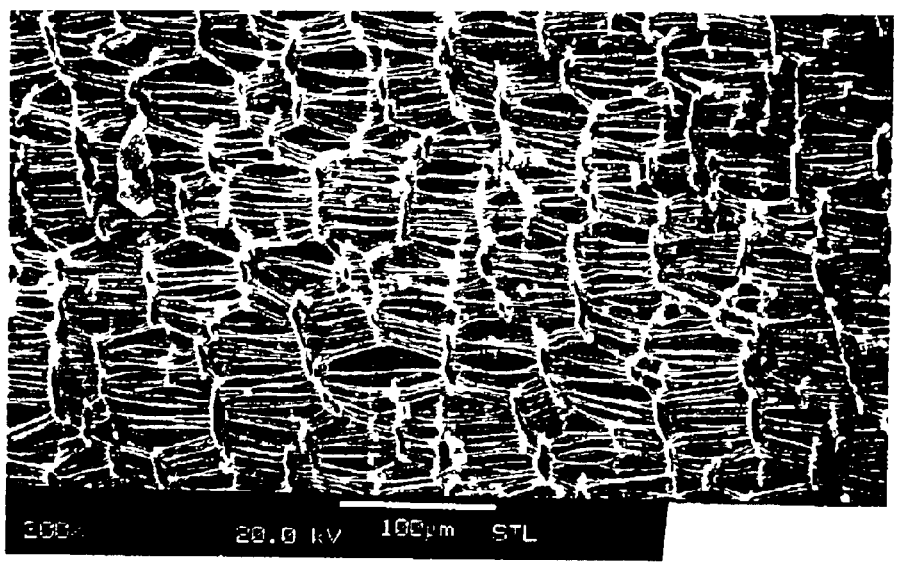
FIG. 19 provides an SEM of an exterior of Sample of the invention.

Sample Q is a graft that is made with the same materials as Sample P, but the highly stretched graft inner layer in an unsintered state is rewet with ISOPAR-H, placed on a mandrel where it is then wrapped with tight porosity ePTFE film. The ISOPAR-H is then run off with heat at either 120° C. for 10 minutes or 200° C. for 3 minutes. A sintered cover is prepared by stretching a second tube over a 10 mm mandrel. The expanded tube is then placed over the wrapped inner layer. The entire assembly is then sintered together. Rewetting results in the inner layer having a reduced porosity when compared to Sample P, see FIGS. 19–21. FIG. 19 shows an exterior of Sample Q, while FIGS. 20 and 21 are interior and cross-sectional views of Sample Q, respectively.

Figure 22:
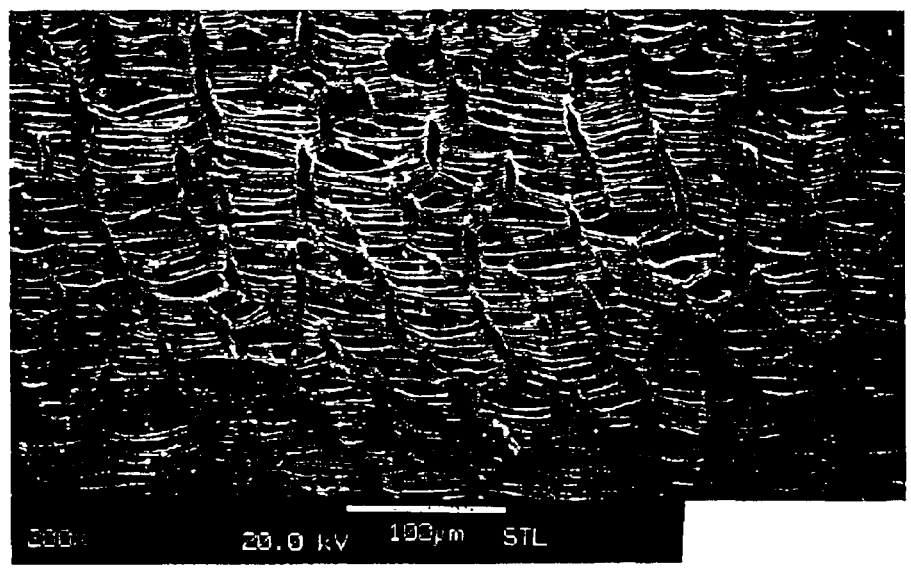
FIG. 22 provides an SEM of an exterior of Sample R of the invention.

Sample R is a graft that is constructed like Sample Q, except that the wrapped inner layer is covered with a non-sintered cover that is wet with ISOPAR-H. The ISOPAR-H is then run off with heat and the entire assembly is then sintered together. See FIGS. 22–24 for views of an exterior, interior and cross-section of Sample R, respectively.

Figure 25:
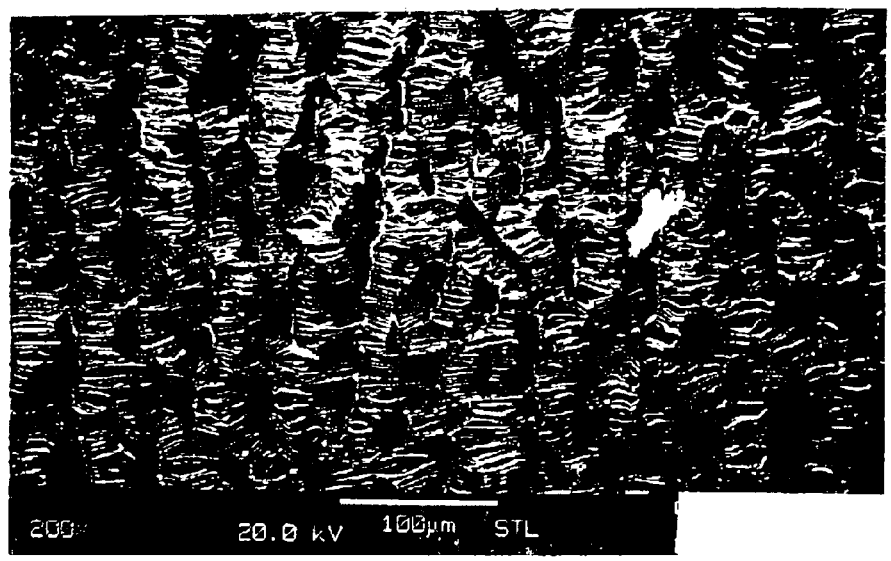
FIG. 25 provides an SEM of an exterior of Sample S of the invention.
Figure 26:
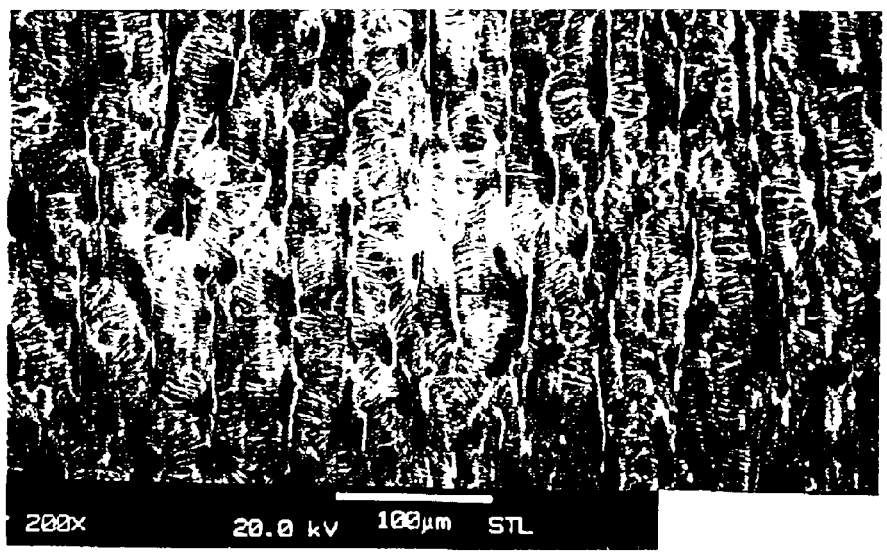
FIG. 26 provides an SEM of an interior of Sample S of the invention.
Figure 27:
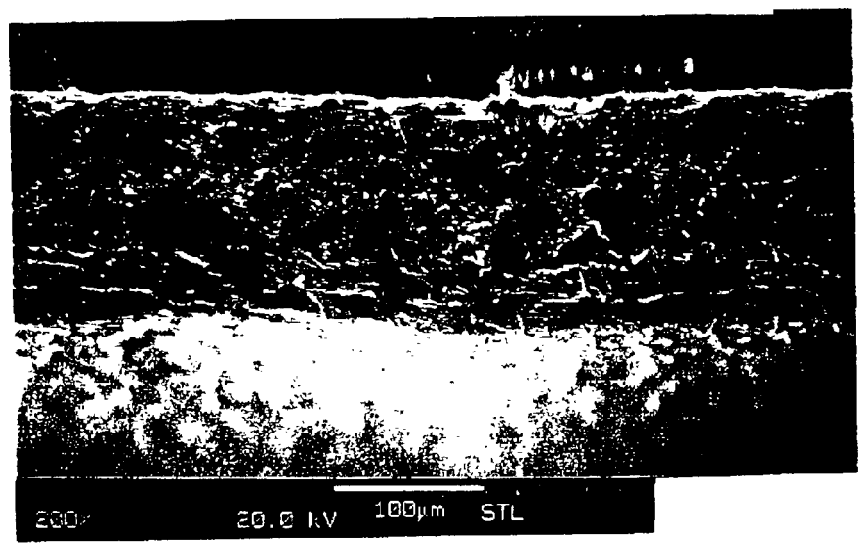
FIG. 27 provides an SEM of a cross-section of Sample S of the invention.

Sample S is a graft that is made with a sintered inner layer that is radially stretched by placement on a mandrel, wrapped and then covered with a non-sintered cover that is wet with ISOPAR-H. The ISOPAR-H is then run off with heat and the entire assembly is then sintered together. See FIGS. 25–27 for an exterior, interior and cross-section of Sample S, respectively.

Figure 20:
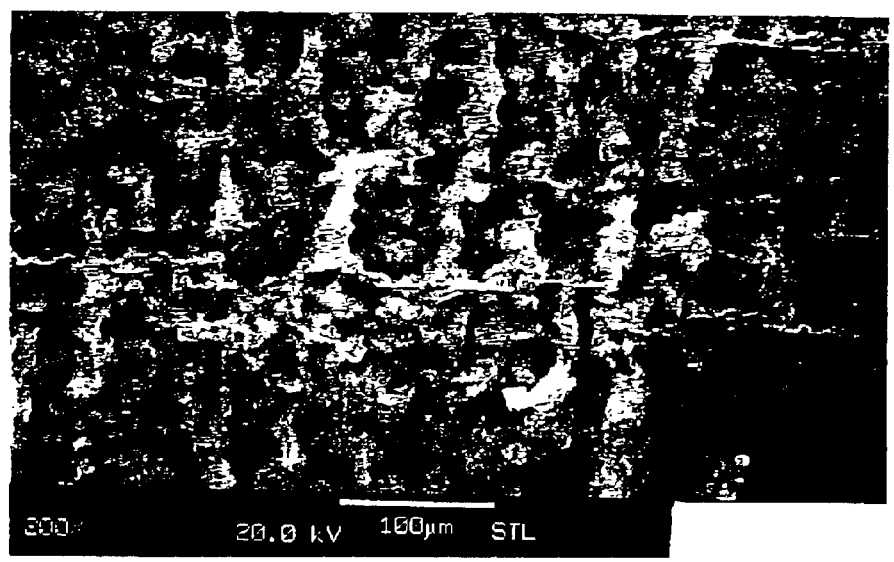
FIG. 20 provides an SEM of an interior of Sample Q of the invention.
Figure 21:
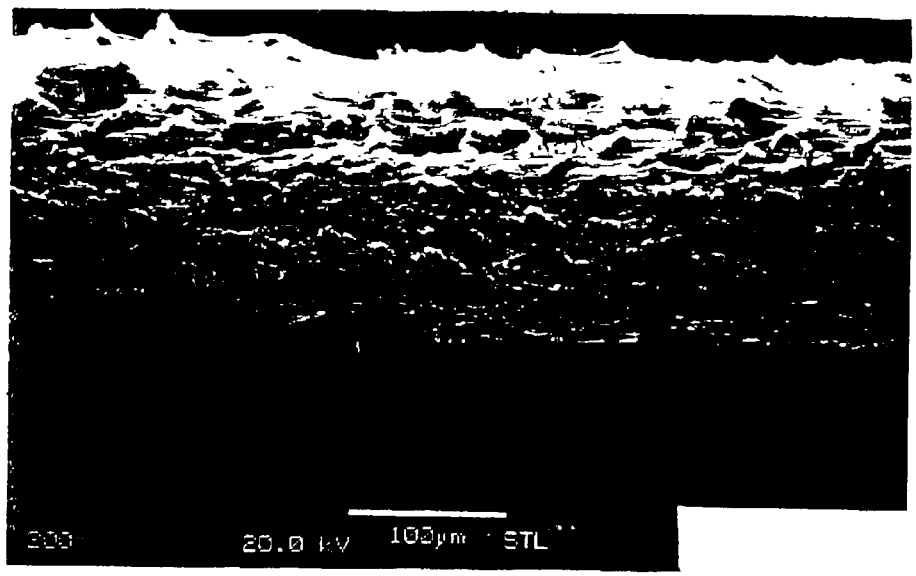
FIG. 21 provides an SEM of a cross-section of Sample Q of the invention.
Figure 23:
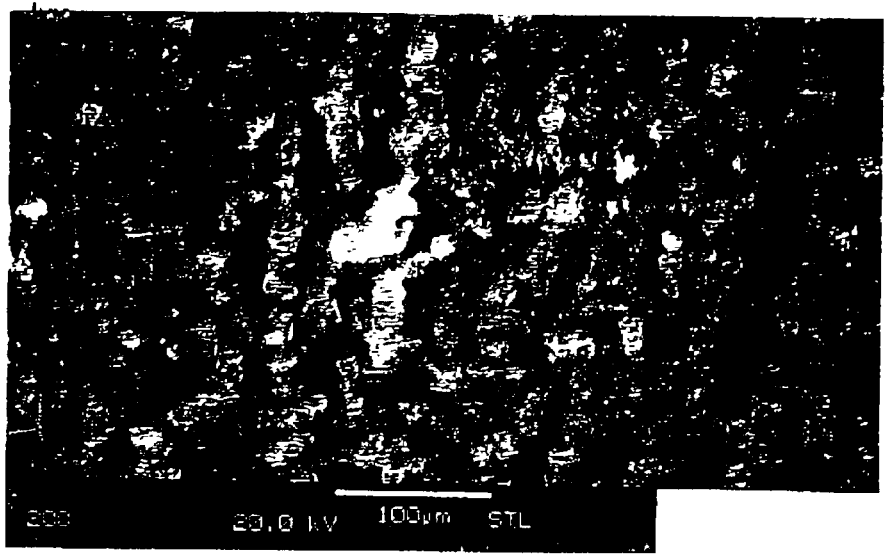
FIG. 23 provides an SEM of an interior of Sample R of the invention.
Figure 24:
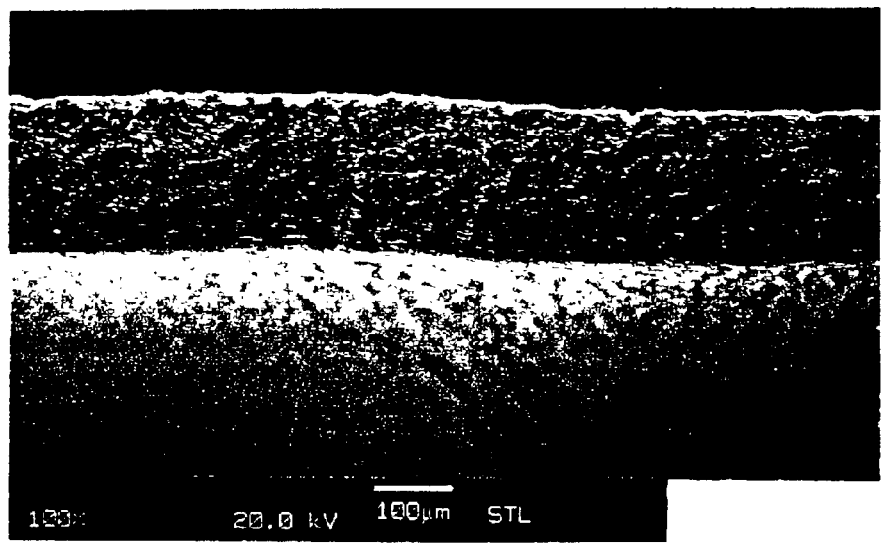
FIG. 24 provides an SEM of a cross-section of Sample R of the invention.

With reference to FIGS. 17, 20 and 23, the samples that were made with the non-sintered method for the inner layer, Samples Q (FIG. 20) and R (FIG. 23) have a very tight inner porosity when compared to the method disclosed in U.S. Pat. No. 5,824,050 (FIG. 17). Samples R and S, made with the wet stretch method for the cover, have higher tear strength values than samples using a sintered cover, Samples P and Q.

Another embodiment of the invention involves the use of a crusher, such as a roller, to crush the inner layer after radial stretching and before application of the ePTFE film, thereby reducing the porosity of the inner layer. Samples T-W illustrate the change in properties from the use of the crusher. Except for crushing, Samples T-W are otherwise processed like Samples P-S, respectively. See Table 6 for comparison.

TABLE 6

| Sample | Inner | Wrap | Outer | Other | LTS (lbf) | RTS (lbf) | SRT (lbf) | Tear (lbf) | Where |
|---|---|---|---|---|---|---|---|---|---|
| P | Sintered | (7.5:1) | Sintered | | 31.7 | 164 | 1.4 | 0.16 | cover |
| Q | Non-Sintered | (7.5:1) | Sintered | | 32.1 | 115 | 0.99 | 0.09 | cover |
| R | Non-Sintered | (7.5:1) | Non-sintered | | 34.1 | 142 | 1.34 | 0.26 | cover |
| S | Sintered | (7.5:1) | Non-sintered | | 33.6 | 153 | 2.1 | 0.26 | cover |

TABLE 6-continued

| Sample | Inner | Wrap | Outer | Other | LTS (lbf) | RTS (lbf) | SRT (lbf) | Tear (lbf) | Where |
|---|---|---|---|---|---|---|---|---|---|
| T | Sintered | (7.5:1) | Sintered | Crusher | 32.8 | 155 | 1.42 | 0.07 | cover |
| U | Non-Sintered | (7.5:1) | Sintered | Crusher | 32.8 | 153 | 1.24 | 0.08 | cover |
| V | Non-Sintered | (7.5:1) | Non-sintered | Crusher | 34.0 | 133 | 0.81 | 0.24 | cover |
| W | Sintered | (7.5:1) | Non-sintered | Crusher | 33.1 | 167 | 2.17 | 0.19 | cover |

The present invention is applicable to a wide variety of product configurations. The following example illustrates an embodiment of the invention involving the application of pressure.

EXAMPLE #8

Figure 28:
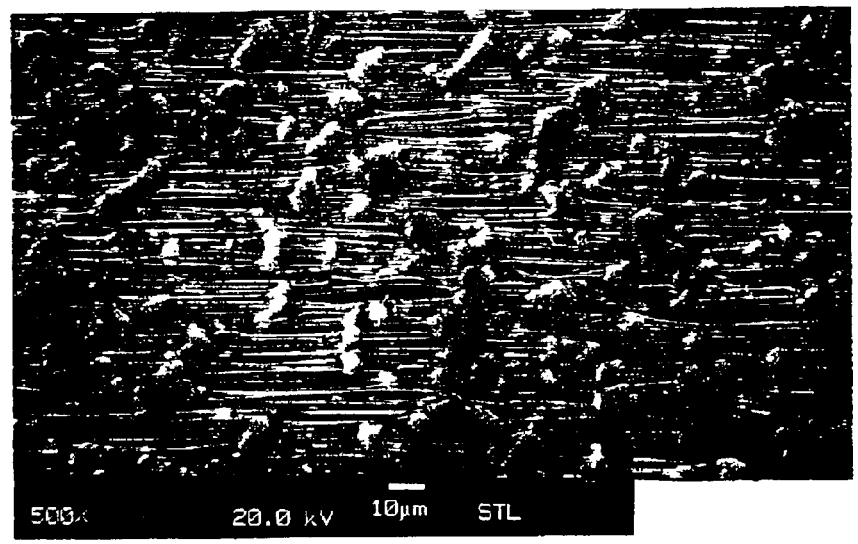
FIG. 28 provides an SEM of Material X.
Figure 29:
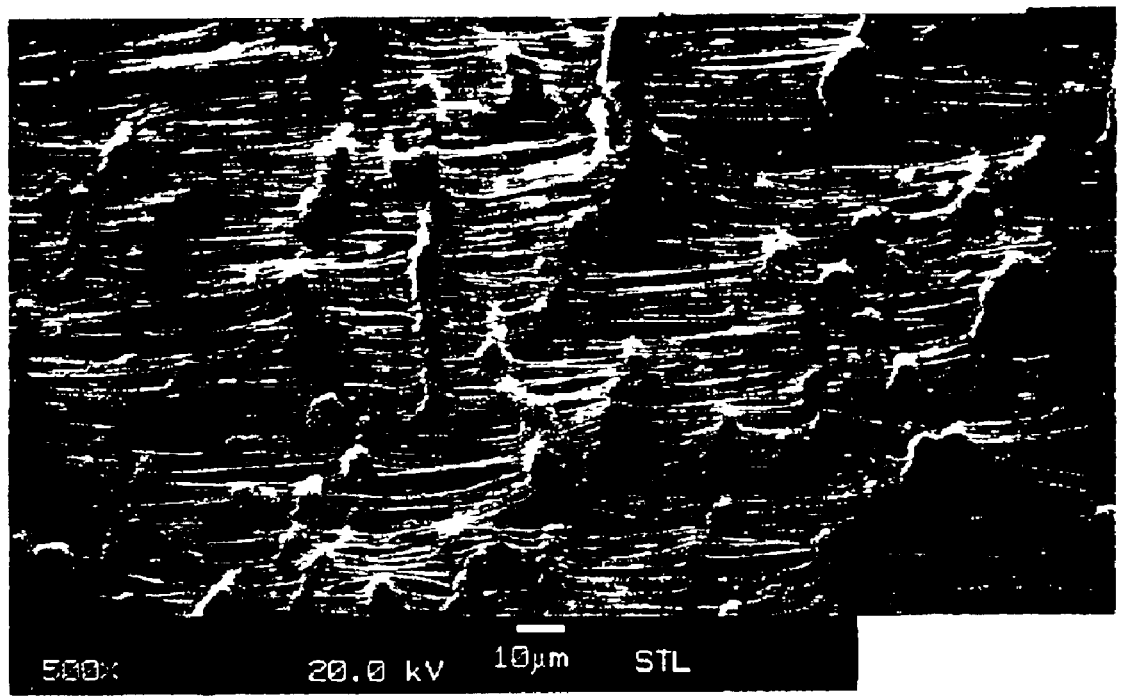
FIG. 29 provides an SEM of Material Y of the invention.

Example 8 of the invention involves a flat material that has pressure applied to it according to the second embodiment of the invention to provide a thin, dense uniform material that has a low porosity. The same lubricated powder of Example 1 is compressed into a cylinder and ram extruded into a flat sheet 6 inches across and 0.040 inches thick. The flat sheet is then compressed through two heated rolls to form a film having a thickness of 5 mil. A first wettable liquid was then removed by passing the film through an oven. The film was then stretched in the machine direction at an elevated temperature to a ratio of 7.5:1 to form Material X, shown in FIG. 28. A roll of Material X was then wet with the ISOPAR-H wettable liquid. Pressure was then applied to the roll of wet material using a set of rollers to form Material Y, Shown in FIG. 29. Material Y has a much higher fibril density than Material X and has a denser overall look to it. Material Y was thinner than Material X, 1.2 mil and 3.1 mil respectively. The density of Material Y was 0.776 g/cm$^3$ compared to Material X which had a density of 0.375 g/cm$^3$.

In addition to the embodiments and examples discussed above, wettable liquid may be applied during initial wetting or rewetting by the use of increased or decreased temperature and/or pressure. Increased or decreased temperature and/or pressure can reduce processing time and enhance the saturation of the expandable polymer.

The following experiments demonstrate the incorporation of a drug or agent into the lubrication/mixing step of processing ePTFE. Several different drugs and delivery systems can be incorporated into ePTFE using the disclosed process.

First, a suitable solvent was chosen. The drug or agent was then formulated into a lubricant, optionally containing a polymer, and a wetting agent. The lubricant was mixed with the PTFE resin, which was then preformed and extruded. The extrudate was then stretched at a temperature that did not damage the drug or agent. This process allows for adjustment of the release profile based on the components that are formulated into the lubricant. This process is capable of forming materials able to deliver drugs or agents in an instant full release, or a more gradual, time controlled release.

EXAMPLE #9

A drug loaded lubricant was first prepared by dissolving Heparin (available from Celsus Labs) in high purity water (NERL). A second solution containing Isopropyl Alcohol 99% and PEG 400 (available from Union Carbide) was also made. The two solutions were then mixed together yielding a lubricant that contained 50% water, 16% PEG 400, 33% Isopropyl Alcohol, and 1% Heparin. PTFE resin (Fluon CD-123 from ICI Americas) was blended with this material to obtain a lubricant level of 25%. The lubricated mix was then performed, extruded, and stretched. Sample "LW100-136A" was stretched to a ratio of 6:1 at 150° C. and 5 IPS, while sample "LW100-136B" was stretched to a ratio of 6:1 at 125° C. and 5 IPS. Samples of the material were then placed in phosphate buffered saline solution (PBS) and incubated at 37° C. overnight. The solution was tested for Heparin using an Azure A analysis. The results of the assay, shown in FIG. 31, indicate that there was Heparin release from the modified ePTFE.

EXAMPLE #10

A lubricant was prepared containing s-nitroso-n-acetyl penicillamine (SNAP) (available from Molecular Probes), a nitric oxide (NO) donor. The drug was first dissolved in dimethyl sulfoxide (DMSO) (available from Sigma) at a concentration of 1 mg/ul. A lubricant was then made by combining 50% ethanol 200 proof (available from Quantum Chemical Corp.), 25% PEG 300 (available from Union Carbide), and 25% Poly DL Lactide-co-Caprolactone 0.091.V. (available from Absorbable Polymer Technologies). The drug solution was then mixed into the lubricant at a level of 10% of total. The drug loaded lubricant was mixed with PTFE resin (Fluon CD-123), available from ICI Americas) at a level of 40%. After the material was mixed, it was set out on a sterile surface overnight to allow the ethanol to evaporate. The resulting mix had a lube level of 25%. The mix was then pre-formed, extruded, and stretched at a temperature of 125° C., a speed of 5 inches per second, and to ratios of 3:1 and 5:1. The loading of a drug in a particular sample was calculated based on the weights of the materials used in processing. The samples were incubated in PBS at 37° C. overnight. The samples were determined to be releasing NO by using a Greiss Assay. Samples made in this example were also tested using cell culture. Samples were cut to 1 mm in length, and weighed. The extrudate was determined to have 3.68 mg of SNAP/mm. The 3:1 stretch ratio had 1.24 mg SNAP/mm. The 5:1 stretch ratio had 0.792 mg of SNAP/mm. Since the NO inhibits cell proliferation, a lower number of cells is an indication of efficacy. The results of this experiment, as seen in FIG. 32, illustrates a does response where higher calculated levels of SNAP yielded a lower number of cells.

EXAMPLE #11

Rapamycin (available from China Chemical Synthesis) was dissolved in ethanol 200 proof (available from Quantum Chemical Corp.) at a concentration of 1 mg/ml. Equal parts of Poly DL Lactide-co-Caprolactone 0.091.V, Methylene Chloride (available from Sigma) and Ethanol 200 Proof were mixed together. The polymer was dissolved in the Methylene chloride prior to adding the Ethanol. Three different levels of Rapamycin solution were then added to separate samples along with a constant amount of DMSO. The drug loaded lubricants were then mixed with PTFE resin (Fluon CD-123) at a level of 20% lube. The samples were then pre-formed, extruded, and stretched to a ratio of 5:1 at 125° C. and 5 inches/second. Samples made in this experiment were tested using cell culture. Samples were cut to 1 mm in length and weighed. The weight of the sample allowed for calculation of the Rapamycin content based on the loading that was used. The samples were tested at different time points by pre-conditioning them in a solution of PBS and Sodium Azide at 37° C. At given time points, the samples were removed from the incubator, washed with sterile water, and placed in cell experiments. Since Rapamycin inhibits cell proliferation, lower number of cells is an indication of efficacy. The results of this example, reported as percent number of cells compared to a blank control are shown in FIG. 33 and illustrate that there is effective Rapamycin release for a period of up to 4 weeks.

EXAMPLE #12

Rapamycin was dissolved in ethanol 200 proof at a concentration of 1 mg/ml. A mixture of 20% Poly DL Lactide-co-Caprolactone 0.43 I.V, 50% Methylene Chloride, and 30% Ethanol 200 Proof was mixed together. The polymer was dissolved in the Methylene Chloride prior to adding the Ethanol. Three different levels of Rapamycin solution were then added to separate samples along with a constant amount of DMSO. The drug loaded lubricants were then mixed with PTFE resin (Fluon CD-123) at a level of 20% lube. The samples were then pre-formed, extruded, and stretched to a ratio of 5:1 at 125° C. and 5 inches per second. Samples made in this experiment were tested using cell culture. Samples were cut to 1 mm in length and weighed. The weight of the sample allowed for calculation of the Rapamycin content based on the loading that was used. The samples were tested at different time points by pre-conditioning them in a solution of PBS and Sodium Azide at 37° C. At given time points, the samples were removed from the incubator, washed with sterile water and placed in cell experiments. Since Rapamycin inhibits cell proliferation, a lower number of cells compared to a blank control as shown in FIG. 34 illustrates that there is effective Rapamycin release for a period of up to 4 weeks.

The drug delivery system can be loaded with concentrations significantly greater than known coating technologies. The lubricant content in the present invention can vary over a relatively large range, for example, from about 3% to about 40% by weight. The drug or agent is loaded during the mixing step according to weight, and is not limited by volume or surface area (as it otherwise would be in conventional immersion or impregnation steps). The drug or agent is being added directly to the finished product, therefore, the drug delivery system can be loaded with drug or agent concentrations of significantly higher amounts.

Further, the release of the drug or agent can occur over relatively longer periods of time. In accordance with the teachings of the present invention, it has been shown that the resulting material can emit a drug or agent for at least a period of about 4 weeks.

The techniques of the present invention may be employed to create implantable prosthetic devices that are adapted for delivery of bioactive materials. For example, vascular grafts with multiple lumens may be created using the techniques described herein. The physical structure components in such prosthetic devices is discussed in further in detail U.S. Pat. No. 5,411,550, entitled "Implantable Prosthetic Device for the Delivery of a Bioactive Material," the contents of which are incorporated herein by reference.

Controlled release systems can be described as including methods for delivering drugs or agents in a controlled manner (i.e., a specific rate of release to a localized or targeted site). Site specific controlled drug delivery can apply an effective concentration of drug or agent to a diseased locale without systemic side affects that often accompany exposure to larger doses of drugs. Patients are exposed to lower overall concentrations of drugs or agents in controlled release systems relative to systemic dosage levels. Furthermore, the drugs and agents are more effective when delivered to the specific locations requiring treatment.

The embodiments of the present invention make use of wettable liquids to form the expanded polymers. These wettable liquids can include drugs and/or other agents that can be used to treat conditions in a controlled and targeted manner.

The extruded article that contains a drug or agent can be processed into a radial and/or longitudinal expanded material using the methods of the present invention. The expanded porous article containing the drug or agent then serves as a means to deliver the drug or agent in a site-specific manner. For example, in the case of vascular grafts, the drug or agent may be a pharmacological agent directed to address infection and/or hyperplasia. In another example, the expanded polymer can be used to form or encompass a stent. In such an instance, the drug or agent can be directed to address restenosis.

Figure 30A:
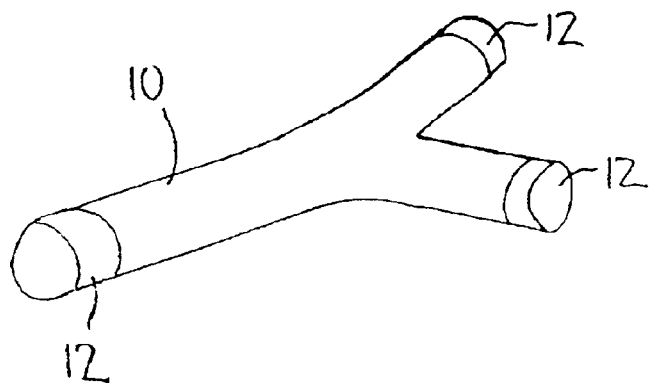
FIGS. 30A, 30B, and 30C illustrate perspective views of example products.

More specficially, as shown in FIG. 30A, an ultra thin wall tube 10 can be produced that can be shaped around a vascular graft 12 in a sleeve or liner fashion, which will release the drug or agent. The vascular graft 12 is formed into a desired graft shape as a part of the wetting and re-wetting process.

Figure 30B:
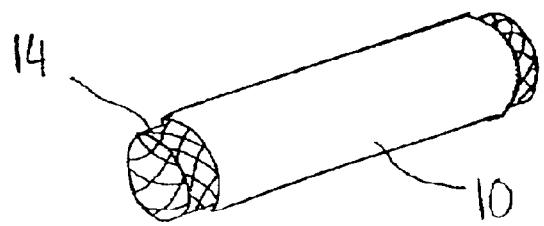
Figure 30C:
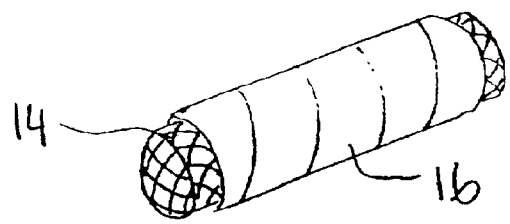

Likewise, as shown in FIG. 30B, the ultra thin wall tube 10 can wrap or slip over a stent 14, and release the drug or agent to the site-specific locale requiring treatment. The thin wall tube 10 is formed using the process of the present invention, and then slipped over a stent 14 structure. Alternatively, if the ultra thin wall is in the form of a wrap, it can wrap around the stent 14, as shown in FIG. 30C.

In example embodiments, expanded polymer materials were made utilizing the wetting and re-wetting process of the present invention. Several of these embodiments were described above as examples herein.

The resulting expanded polymer was then placed in simulated conditions for placement within a patient body and the amount of Heparin emitted from the expanded polymer was measured over a period of time. The results were also provided in example illustrations herein.

The inclusion of a drug or agent in the expanded polymer as made possible by the method of the present invention eliminates, or at least greatly reduces, systemic responses associated with traditional oral or intravenous therapies. The minimization of drug permeability effects through tissue results from the ability to target the application of the drug or agent to specific locales. The ability to incorporate the drug or agent in the expanded polymer makes it possible to load the drug delivery system with concentrations significantly greater than known coating technologies. Further, the release of the drug or agent can occur over longer periods of time. The use of the expanded polymer including the drug or agent provides a material that is radially expandable without splitting or breakage.

Expandable polymers of the present invention have wide ranging applications, such as devices for in vivo implantation, prostheses intended for placement or implantation to supplement or replace a segment of a natural biological blood vessel, and supports for tissue repair, reinforcement or augmentation. Specific products include but are not limited to heart valves, sutures, vascular access devices, vascular grafts, shunts and catheters. Other products include single and multilayered membranes. Multilayered membranes containing regions of selective porosity and chemistry are useful in the medical diagnostic and the filtration industries. For example, some clinical diagnostic test strips contain multilayer membranes with selective binding sites in each layer to capture analytes from blood, serum, and the like, when the test liquid is flowing through it.

According to additional aspects of the invention, expandable polymers may be formed into sheets, grafts, electrical insulation and other known polymer applications. These applications include among other devices, vascular grafts, endovascular liners and grafts, prosthetic patches, vascular access devices, shunts, catheters, sutures or implantable tissue augmentation devices, such as those used in cosmetic surgery. According to yet a further feature, the articles of manufacture include single and multilayered membranes formed from sheets. Such membranes may be employed in clinical diagnostic test strips or in filtration devices.

The invention can be applied to other processes where stretching or expanding of material is involved. It will thus be seen that the invention efficiently attains the objects set forth above, including providing implantable devices having tailored porosity and/or chemistry characteristics. Since certain changes may be made in the above constructions and the described methods without departing from the scope of the invention, it is intended that all matter contained in the above description or shown in the accompanying drawings be interpreted as illustrative and not in a limiting sense. By way of example, any known methods for varying the porosity and/or chemistry characteristics of implantable prostheses, such as varying the lubrication level in the blended pasted, viewed in combination with the disclosed methods are considered to be within the scope of the present invention. Additionally, any methods for combining resins, pastes, billets or extrudates, according to the methods of the invention, are also considered to be within the scope of the present invention.

Having described the invention, what is claimed as new and protected by Letters Patent is:

1. A method for forming an article, comprising the steps of:
   mixing an expandable polymer resin with a first wettable liquid and at least one of a drug and an agent to form a mixture;
   extruding said mixture to form an extruded article; and
   rewetting said extruded article with a second wettable liquid to form a wetted material;
   wherein at least one of the polymer resin, the first wettable liquid, and the second wettable liquid is formed at least partially of at least one of the drug and the agent.

2. The method of claim 1, wherein said step of rewetting occurs at a temperature below the boiling temperature of said second wettable liquid.

3. The method of claim 1, wherein said first and second wettable liquids are the same composition.

4. The method of claim 1, further comprising, the step of stretching said extruded article after said step of extruding.

5. The method of claim 4, further comprising the step of removing said first wettable liquid prior to said step of stretching said extrude article.

6. The method of claim 5, further comprising, the step of stretching said wetted material after said step of rewetting.

7. The method of claim 6, further comprising the step of removing said second wettable liquid from said wetted material to form a dried material.

8. The method of claim 7, further comprising the step of stretching said dried material, after said step of removing said second wettable liquid.

9. The method of claim 6, wherein said step of stretching said wetted material is performed at a temperature less than 80° F.

10. The method of claim 6, further comprising, after said step of stretching said wetted material, the steps of:
    removing said second wettable liquid from said wetted material to form a dried material; and
    stretching said dried material.

11. The method of claim 1, further comprising, the step of stretching said wetted material, after said step of rewetting.

12. The method of claim 11, wherein said step of stretching said wetted material is performed at a temperature less than 80° F.

13. The method of claim 1, wherein said article is in the shape of a tube or a flat sheet.

14. The method of claim 1, wherein said expandable polymer is a fluoropolymer or a polyolefin.

15. The method of claim 1, wherein the drug and the agent comprise at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, and-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

16. The method of claim 1, wherein said first wettable liquid is formed at least partially of at least one of a drug and an agent.

17. The method of claim 1, wherein said second wettable liquid is formed at least partially of at least one of a drug and an agent.

18. The method of claim 1, wherein said first wettable liquid and said second wettable liquid are formed at least partially of at least one of a drug and an agent.

19. The method of claim 1, further comprising mixing a powder formed at least partially of at least one of a drug and an agent to form the polymer resin.

20. A method of forming an article from an expandable polymer, comprising the steps of:
    rewetting said expandable polymer with a wettable liquid to form a wetted material, at least one of the wettable liquid and the expandable polymer being formed at least partially of at least one of a drug and an agent; and
    stretching said wetted material.

21. A method for forming an article, comprising the steps of:
    mixing an expandable polymer resin with a first wettable liquid to form a mixture;
    extruding said mixture to form an extruded article;
    calendaring said extruded article;
    removing said first wettable liquid from said extruded article to form a first dried material;
    stretching said first dried material;

rewetting said first dried material with a second wettable liquid to form a wetted material;

applying pressure to said wetted material;

removing said second wettable liquid to form a second dried material; and stretching said second dried material;

wherein at least one of said first wettable liquid, said second wettable liquid, and said polymer resin is formed at least partially of at least one of a drug and an agent.

22. A method for forming a coated graft, comprising the steps of:

mixing an expandable polymer resin with a first wettable liquid to form a mixture;

extruding said mixture to form an extruded article;

rewetting said extruded article with a second wettable liquid to form a wetted material; and covering a graft structure with the expandable polymer resin to form the coated graft;

wherein at least one of said first wettable liquid, said second wettable liquid, and said polymer resin is formed at least partially of at least one of a drug and an agent.

23. The method of claim 22, wherein the expandable polymer resin is formed in the shape of the graft structure and slips over the graft structure to form the coated graft.

24. A method for forming a coated stent, comprising the steps of:

mixing an expandable polymer resin with a first wettable liquid to form a mixture;

extruding said mixture to form an extruded article;

rewetting said extruded article with a second wettable liquid to form a wetted material;

covering a stent structure with the expandable polymer resin to form the coated graft;

wherein at least one of said first wettable liquid, said second wettable liquid, and said polymer resin is formed at least partially of at least one of a drug and an agent.

25. The method of claim 24, wherein the expandable polymer resin is formed in the shape of the stent structure and slides over the stunt structure to form the coated stent.

26. The method of claim 24, wherein the expandable polymer is formed in the shape of a wrap and is wrapped about the stent structure to form the coated stent.

27. A method for forming an article, comprising:

combining at least one of a drug and an agent with a first wettable liquid;

mixing a polymer resin with the first wettable liquid to farm a mixture;

forming a pre-form from the mixture; and extruding the pre-form to form the article.

28. The method according to claim 27, wherein said article is in the shape of a tube or a flat sheet.

29. The method according to claim 27, wherein said at least one of a drug and an agent selected from the group consisting of at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

30. The method according to claim 27, wherein said first wettable liquid is formed of at least one of a drug and an agent.

31. The method according to claim 27, further comprising mixing a powder formed at least partially of at least one of a drug and an agent to form said polymer resin.

32. A method for forming an article, comprising:

combining at least one of a drug and an agent with a first wettable liquid;

mixing a polymer resin with the first wettable liquid to form a mixture;

forming a pre-form from the mixture;

extruding the pre-form to form an extruded article; and stretching the extruded article to form the article.

33. The method according to claim 32, wherein said article is in the shape of a tube or a flat sheet.

34. The method according to claim 32, wherein said at least one of a drug and an agent selected from the group consisting of at least one antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

35. The method according to claim 32, wherein said first wettable liquid is formed of at least one of a drug and an agent.

36. The method according to claim 32, further comprising mixing a powder formed at least partially of at least one of a drug and an agent to form said polymer resin.

37. A method for forming an article, comprising:

combining at least one of a drug and an agent with a first wettable liquid;

mixing a polymer resin with the first wettable liquid to form a mixture;

forming a pre-form from the mixture;

extruding the pre-form to form an extruded article;

drying the extruded article; and stretching the extruded article to form the article.

38. The method according to claim 37, wherein said article is in the shape of a tube or a flat sheet.

39. The method according to claim 37, wherein said at least one of a drug and an agent selected from the group consisting of at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

40. The method according to claim 37, wherein said first wettable liquid is formed of at least one of a drug and an agent.

41. The method according to claim 37, further comprising mixing a powder formed at least partially of at least one of a drug and an agent to form said polymer resin.

42. A method for forming an article, comprising:
combining at least one of a drug and an agent with a first wettable liquid;
mixing a polymer resin with the first wettable liquid to form a mixture;
forming a pre-form from the mixture;
extruding the pre-form to form an extruded article;
re-wetting the extruded article with at least one of the first wettable liquid and a second wettable liquid; and
stretching the re-wetted and extruded article to form the article.

43. The method according to claim 42, wherein said stretching of said extruded article is performed a temperature below a boiling point of the second wettable liquid.

44. The method according to claim 42, wherein said article is in the shape of a tube or a flat sheet.

45. The method according to claim 42, wherein said at least one of a drug and an agent selected from the group consisting of at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

46. The method according to claim 42, wherein at least one of said first wettable liquid and said second wettable liquid is formed of at least one of a drug and an agent.

47. The method according to claim 42, further comprising mixing a powder formed at least partially of at least one of a drug and an agent to form said polymer resin.

48. A method for forming an article, comprising:
combining at least one of a drug and an agent with a first wettable liquid;
mixing a polymer resin with the first wettable liquid to form a mixture;
forming a pre-form from the mixture;
extruding the pre-form to form an extruded article;
stretching the extruded article; and
re-wetting the extruded article with a second wettable liquid to form the article.

49. The method according to claim 48, wherein said stretching of said extruded article is performed at a temperature below a boiling point of the second wettable liquid.

50. The method according to claim 48, wherein said article is in the shape of a tube or a flat sheet.

51. The method according to claim 48, wherein said at least one of a drug and an agent selected from the group consisting of at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

52. The method according to claim 48, wherein at least one of said first wettable liquid and said second wettable liquid as formed of at least one of a drug and an agent.

53. The method according to claim 48, further comprising mixing a powder formed at least partially of at least one of a drug and an agent to form said polymer resin.

54. A method for forming an article, comprising:
combining at least one of a drug and an agent with a first wettable liquid;
mixing a polymer resin with the first wettable liquid to form a mixture;
forming a pre-form from the mixture;
extruding the pre-form to form an extruded article;
stretching the extruded article;
re-wetting the extruded article with a second wettable liquid; and
stretching the re-wetted extruded article to form the article.

55. The method according to claim 54, wherein said stretching of said extruded article is performed at a temperature below a boiling point of the second wettable liquid.

56. The method according to claim 54, wherein said article is in the shape of a tube or a flat sheet.

57. The method according to claim 54, wherein said at least one of a drug and an agent selected from the group consisting of at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

58. The method according to claim 54, wherein at least one of said first wettable liquid and said second wettable liquid is formed of at least one of a drug and an agent.

59. The method according to claim 54, further comprising mixing a powder formed at least partially of at least one of a drug and an agent to form said polymer resin.

* * * * *